United States Patent
Herr et al.

(10) Patent No.: US 11,504,530 B2
(45) Date of Patent: Nov. 22, 2022

(54) TRANSDERMAL OPTOGENETIC PERIPHERAL NERVE STIMULATION

(71) Applicant: MASSACHUSETTS INSTITUTE OF TECHNOLOGY, Cambridge, MA (US)

(72) Inventors: Hugh M. Herr, Somerville, MA (US); Benjamin Maimon, Brookline, MA (US); Anthony Zorzos, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 608 days.

(21) Appl. No.: 16/344,866

(22) PCT Filed: Oct. 31, 2017

(86) PCT No.: PCT/US2017/059247
§ 371 (c)(1),
(2) Date: Apr. 25, 2019

(87) PCT Pub. No.: WO2018/085253
PCT Pub. Date: May 11, 2018

(65) Prior Publication Data
US 2020/0046968 A1 Feb. 13, 2020

Related U.S. Application Data

(60) Provisional application No. 62/415,817, filed on Nov. 1, 2016.

(51) Int. Cl.
| | | |
|---|---|---|
| *A61N 1/32* | (2006.01) | |
| *A61K 9/00* | (2006.01) | |
| *A61N 1/04* | (2006.01) | |
| *A61N 5/06* | (2006.01) | |
| *C07K 14/47* | (2006.01) | |
| *C12N 15/86* | (2006.01) | |
| *A61N 5/067* | (2006.01) | |
| *A61B 5/11* | (2006.01) | |

(52) U.S. Cl.
CPC ............ *A61N 1/327* (2013.01); *A61K 9/0009* (2013.01); *A61K 9/0019* (2013.01); *A61N 1/0412* (2013.01); *A61N 5/062* (2013.01); *A61N 5/0622* (2013.01); *C07K 14/47* (2013.01); *C12N 15/86* (2013.01); *A61B 5/1126* (2013.01); *A61B 2562/0219* (2013.01); *A61N 5/067* (2021.08); *A61N 2005/0645* (2013.01); *A61N 2005/0651* (2013.01); *A61N 2005/0659* (2013.01); *A61N 2005/0661* (2013.01); *A61N 2005/0663* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 2009/0093761 A1* | 4/2009 | Sliwa | A61M 5/427 604/116 |
| 2011/0144723 A1 | 6/2011 | Streeter et al. | |
| 2014/0324138 A1 | 10/2014 | Wentz et al. | |
| 2016/0175611 A1 | 6/2016 | Kim et al. | |

FOREIGN PATENT DOCUMENTS

| | | |
|---|---|---|
| WO | 2007/024391 A2 | 3/2007 |
| WO | 2012/061684 A1 | 5/2012 |
| WO | 2015/200380 A1 | 12/2015 |

OTHER PUBLICATIONS

Iyer, S. M. et al. Virally mediated optogenetic excitation and inhibition of pain in freely moving nontransgenic mice. Nat. Biotechnol. 32, 274-8 (2014).
Llewellyn, M. E., Thompson, K. R., Deisseroth, K. & Delp, S. L. Orderly recruitment of motor units under optical control in vivo. Nat. Med. 16, 1161-1165 (2010).
Ye, H., Daoud-El Baba, M., Peng, R.-W. & Fussenegger, M. A synthetic optogenetic transcription device enhances blood-glucose homeostasis in mice. Science 332, 1565-1568 (2011).
Bickel, C. S., Gregory, C. M. & Dean, J. C. Motor unit recruitment during neuromuscular electrical stimulation: A critical appraisal. European Journal of Applied Physiology 111, 2399-2407 (2011).
Towne, C., Montgomery, K. L., Iyer, S. M., Deisseroth, K. & Delp, S. L. Optogenetic control of targeted peripheral axons in freely moving animals. PLoS One 8, e72691 (2013).
Ji, Z.-G. et al. Light-evoked Somatosensory Perception of Transgenic Rats That Express Channelrhodopsin-2 in Dorsal Root Ganglion Cells. PLoS One 7, e32699 (2012).
Jacques, S. L. Optical properties of biological tissues: a review. Phys. Med. Biol. 58, R37-61 (2013).
Kapur, S., Richner, T., Brodnick, S., Williams, J. & Poore, S. Development of an Optogenetic Sensory Peripheral Nerve Interface. Plast. Surg. Res. Counc. (2014).
Ayling, O. G. S., Harrison, T. C., Boyd, J. D., Goroshkov, A. & Murphy, T. H. Automated light-based mapping of motor cortex by photoactivation of channelrhodopsin-2 transgenic mice. Nat. Methods 6, 219-224 (2009).

(Continued)

*Primary Examiner* — Robert M Kelly
(74) *Attorney, Agent, or Firm* — Hamilton, Brook, Smith & Reynolds, P.C.

(57) ABSTRACT

A nerve in a mammal is optogenetically transduced, wherein the nerve is susceptible to stimulus by selective application of transdermal light, and a light source is applied to dermis of the mammal at or proximate to the optogenetically transduced nerve, to thereby stimulate the nerve. A wearable device for optogenetic motor control and sensation restoration of a mammal includes a wearable support, a power source at the wearable support, a controller at the wearable support and in electrical communication with a power source, and a transdermal light source coupled to the controller.

10 Claims, 18 Drawing Sheets

(56) References Cited

OTHER PUBLICATIONS

Chuong, A. S. et al. Noninvasive optical inhibition with a red-shifted microbial rhodopsin. Nat. Neurosci. 17, 1123-9 (2014).

Lin, J. Y., Knutsen, P. M., Muller, A., Kleinfeld, D. & Tsien, R. Y. ReaChR: a red-shifted variant of channelrhodopsin enables deep transcranial optogenetic excitation. Nat. Neurosci. 16, 1499-508 (2013).

Kim, T., Folcher, M., Baba, M. D.-E. & Fussenegger, M. A Synthetic Erectile Optogenetic Stimulator Enabling Blue-Light-Inducible Penile Erection. Angew. Chemie Int. Ed. 54, 5933-5938 (2015).

Magown, P., Shettar, B., Zhang, Y. & Rafuse, V. F. Direct optical activation of skeletal muscle fibres efficiently controls muscle contraction and attenuates denervation atrophy. Nat. Commun. 6, 8506 (2015).

Peterson, E. J. & Tyler, D. J. Motor neuron activation in peripheral nerves using infrared neural stimulation. J. Neural Eng. 11, 016001 (2013).

Bashkatov, A. N., Genina, E. A. & Tuchin, V. V. Optical Properties of Skin, Subcutaneous, and Muscle Tissues: A Review. J. Innov. Opt. Health Sci. 04, 9-38 (2011).

Yaroslavsky, A. N. et al. Optical properties of selected native and coagulated human brain tissues in vitro in the visible and near infrared spectral range. Phys. Med. Biol. 47, 305 (2002).

Islam, M. S. et al. Extracting structural features of rat sciatic nerve using polarization-sensitive spectral domain optical coherence tomography. J. Biomed. Opt. 17, 056012 (2012).

Hendriks, B. H. W. et al. Nerve detection with optical spectroscopy for regional anesthesia procedures. J. Transl. Med. 13, 380 (2015).

Welch, A. J. & Van Gemert, M. J. C. Optical-thermal response of laser-irradiated tissue. Optical-Thermal Response of Laser-Irradiated Tissue, 2nd ed, pp. 915-939 (2011).

McCartney, C. J. L., Xu, D., Constantinescu, C., Abbas, S. & Chan, V. W. S. Ultrasound examination of peripheral nerves in the forearm. Reg. Anesth. Pain Med. 32, 434-9, (2007).

Honjoh, T. et al. Optogenetic Patterning of Whisker-Barrel Cortical System in Transgenic Rat Expressing Channelrhodopsin-2. PLoS One 9, e93706 (2014).

Cheever, T. R., Olson, E. A. & Ervasti, J. M. Axonal regeneration and neuronal function are preserved in motor neurons lacking β-Actin In Vivo. PLoS One 6, (2011).

Montgomery, K. L. et al. Beyond the brain: Optogenetic control in the spinal cord and peripheral nervous system. Sci. Transl. Med. 8, 337rv5 (2016).

Bainbridge, J. W. B. et al. Long-Term Effect of Gene Therapy on Leber's Congenital Amaurosis. http://dx.doi.org/10.1056/NEJMoa1414221 (2015).

Mingozzi, F. et al. Immune responses to AAV vectors: overcoming barriers to successful gene therapy. Blood 122, 23-36 (2013).

Sack, B. K. & Herzog, R. W. Evading the immune response upon in vivo gene therapy with viral vectors. Curr. Opin. Mol. Ther. 11, 493-503 (2009).

Mason, M. R. et al. Comparison of AAV Serotypes for Gene Delivery to Dorsal Root Ganglion Neurons. Mol. Ther. 18, 715-724 (2010).

Department of Health and Human Services. Memorandum: "Premarket Approval of Neurocontrol Freehand System® Action." Aug. 15, 1997.

Williams, E. K. et al. Sensory Neurons that Detect Stretch and Nutrients in the Digestive System. Cell 166, 209-221 (2016).

Chang, R. B., Strochlic, D. E., Williams, E. K., Umans, B. D. & Liberles, S. D. Vagal Sensory Neuron Subtypes that Differentially Control Breathing. Cell 161, 622-33 (2015).

Grosenick, L., Marshel, J. H. & Deisseroth, K. Closed-Loop and Activity-Guided Optogenetic Control. Neuron 86, 106-139 (2015).

International Search Report for International Application No. PCT/US2017/059247, entitled "Transdermal Optogenetic Peripheral Nerve Stimulation." dated May 19, 2019.

International Preliminary Report on Patentability and Written Opinion for International Application No. PCTUS2017/059247, entitled "Transdermal Optogenetic Peripheral Nerve Stimulation." dated May 16, 2019.

International Search Report and Written Opinion for International Application No. PCT/US2017/059247, entitled "Transdermal Optogenetic Peripheral Nerve Stimulation." dated Feb. 23, 2018.

International Search Report for International Application No. PCT/US2017/059247, entitled "Transdermal Optogenetic Peripheral Nerve Stimulation." dated Feb. 23, 2018.

* cited by examiner

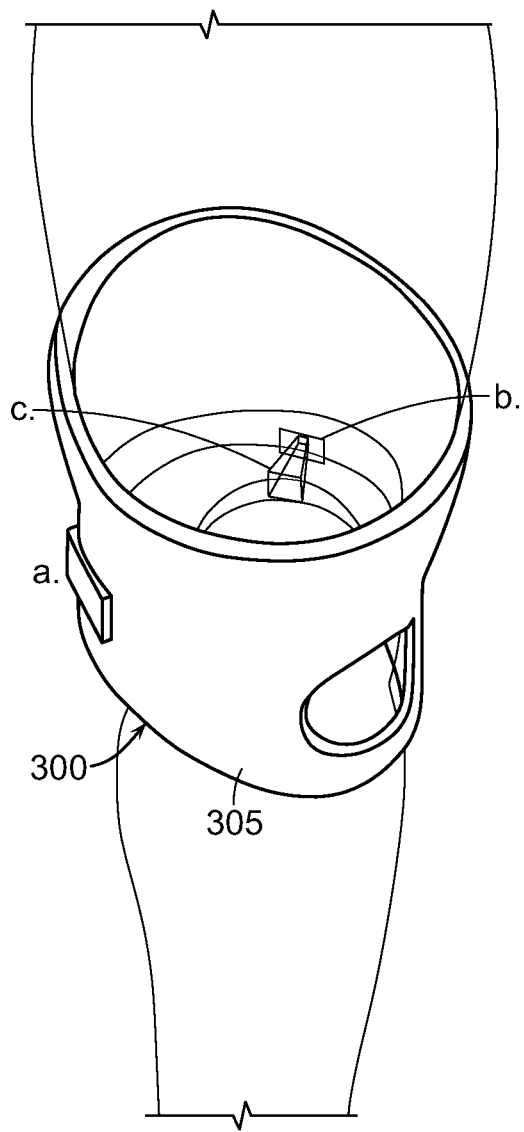
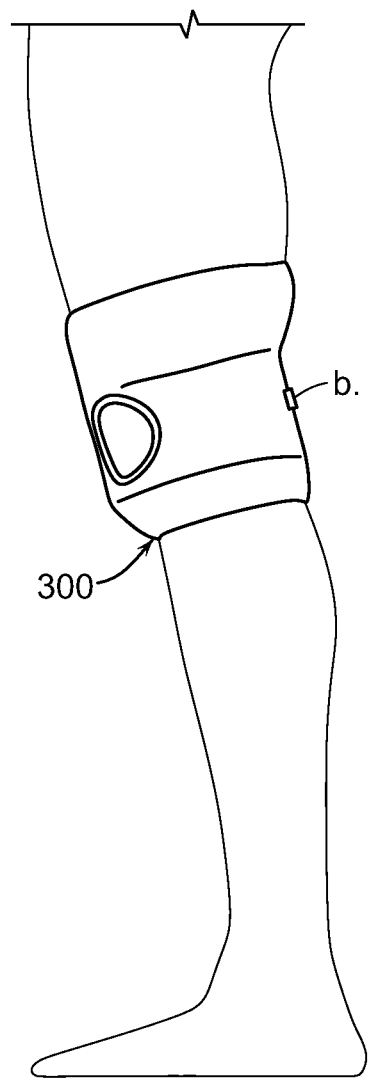
FIG. 3A
FIG. 3B

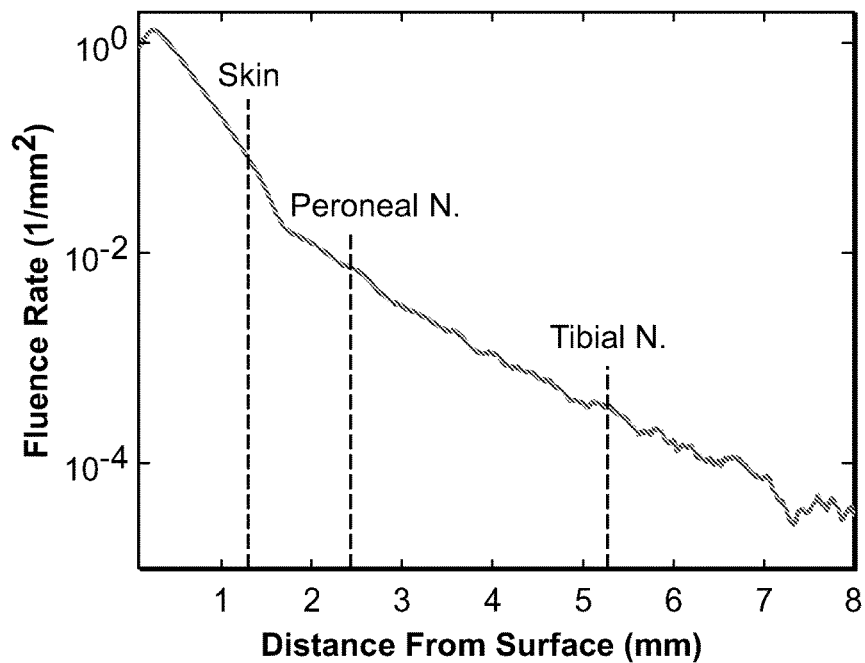
FIG. 15
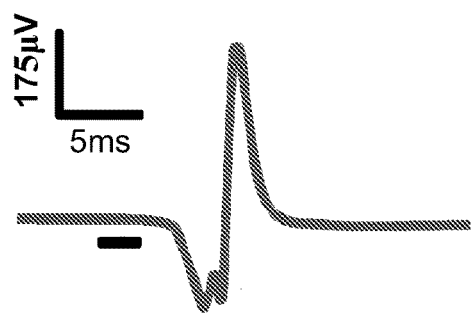
FIG. 16
FIG. 17

TRANSDERMAL OPTOGENETIC PERIPHERAL NERVE STIMULATION

RELATED APPLICATIONS

This application is the U.S. National Stage of International Application No. PCT/US2017/059247, filed Oct. 31, 2017, which designates the U.S., published in English, and claims the benefit of U.S. Provisional Application No. 62/415,817, filed Nov. 1, 2016. The entire teachings of the above applications are incorporated herein by reference.

BACKGROUND OF THE INVENTION

Optogenetic techniques have recently been applied to peripheral nerves as a scientific tool with the translatable goal of alleviating a variety of disorders, including chronic pain[1], muscle fatigue[2], glucose-related pathologies[3], and others. When compared to the electrical stimulation of peripheral nerves, there are numerous advantages: the ability to target molecularly defined subtypes, access to opsins engendering neural inhibition, and optical recruitment of motor axons in a fashion that mimics natural recruitment[2], which eliminates the fatigue roadblock inherent to functional electrical stimulation (FES)[4].

The retrograde transfection of AAV6-hSyn-ChR2-YFP, injected intramuscularly, has been shown to result in a repeatable muscle activation in response to direct optical stimulation of the peroneal and tibial nerves[5]. Direct illumination was accomplished using several different invasive techniques: the exposed nerve illuminated with a free-space optical source[5], an LED-based optical nerve cuff[2], and a fiber-optic-based optical nerve cuff[5]. These invasive methods were relied upon to provide a sufficiently high fluence rate to activate the target opsins expressed in the nerves. A transdermal illumination approach was successfully pursued for suppressing pain receptors in mice via stimulation of superficial cutaneous nociceptors[1]. Transdermal illumination has been postulated to target pain and touch fibers due to their superficial nature; deep-tissue targets were previously considered optically inaccessible because of the significant attenuation of blue light in biological tissue[6,7]. Transdermal stimulation of sensory axons in the sciatic nerve of transgenic mice has been previously linked to cortical recordings, yet it is unclear the extent to which cutaneous co-activation affected the measurements[8].

There have been several optogenetics studies leveraging non-invasive illumination in the brain. Both trans-cortical optical stimulation of ChR2-expressing neurons[9] and trans-cortical neural silencing using the red-shifted opsin Jaws[10] could reliably activate and inhibit neural populations respectively, the latter due to the improved penetration of red light in tissue; both experiments, however, required a fiber implant beneath the skin. Recent work in the vibrissa motor cortex of an awake, head-fixed mouse demonstrated optogenetic stimulation through bone and skin using both the red-light opsin ReaChR and ChR2, although the degree of movement was superior with ReaChR, which could produce reliable vibrissa motions up to 10 mm from the skin surface[11]. Direct transdermal optogenetic control of smooth muscle in rats[12] and skeletal muscle in transgenic mice[13] has been demonstrated. However, nerve targets are smaller and deeper than muscle targets, and represent a greater challenge to the transdermal approach. Infrared neural stimulation has also been presented as a promising optogenetics alternative that may theoretically produce anatomically selective, transdermal stimulation without modification of target tissue. However, major concerns include heating-induced tissue damage, non-selective co-stimulation of sensory and motor fibers, and difficulty localizing the target nerves[14].

However, peripheral nerves are located beneath several tissue types, including skin, blood vessels, adipose tissue, and muscle. These tissues strongly attenuate visible light, preventing the majority of delivered light from reaching the target nerve.

SUMMARY OF THE INVENTION

The invention generally is directed to a method of stimulating a nerve of mammal, and to a wearable device for optogenetic motor control and restoring sensation in a mammal.

In one embodiment, the invention is a method of stimulating a nerve of a mammal, including the steps of optogenetically transforming a nerve in a mammal, wherein the nerve is susceptible to stimulation by selective application of transdermal light, and applying a light source to dermis of the mammal proximate to the optogenetically transduced nerve, thereby stimulating the nerve.

In another embodiment, the invention is a method optogenetically transfecting a mammal, including the step of administering to selected tissue of the mammal genetic material encoding light-sensitive opsins and a neural promoter, wherein the genetic material causes a transdermal optogenetic peripheral nervous system response to light.

In still another embodiment, the invention is a wearable device for optogenetic motor control and restoring sensation of a mammal, including a wearable support, a power source at the wearable support, a controller at the wearable support and in electrical communication with the power source, and a transdermal light source coupled to the controller, the controller driving a light source to direct light from the wearable support and toward the mammal while wearing the support.

The inventors have discovered that, by injecting a higher overall number of viral particles, more viral copies integrate in the motor neuron genome, thereby translating to a higher density of ChR2 channels in the axon and a sufficiently high optical sensitivity, whereby transdermal, optogenetic control of nerves is possible. Opsin expression levels and muscle response are demonstrated to be a function of injected viral particles (vp) and fluence rate in a rat model.

This invention has several advantages. For example, the method of the invention can be employed in the treatment of spinal cord injury, post-polio syndrome, ALS, or other type of CNS-mediated loss of motor function; for neural inhibition, such as can be employed to control chronic pain from the spinal cord nerves, cranial nerves (such as trigeminal neuralgia), or other etiologies. Intra-nerve injections of high-concentration AAV into nerve stumps could produce optogenetically active nerves that can be employed in the method to improve the functionality of current prosthetic devices by providing the much needed "sense of touch" feedback to amputees from their electromechanical devices. The method of the invention can also be employed to treat foot-drop, which is a condition in stroke victims characterized by the inability of the patient to dorsiflex during swing phase, resulting in the toes dragging along the ground. Mood disorders, such as depression and epilepsy, can be treated by the invention, by selective stimulation of molecularly unique genetically-defined axonal subsets of the vagus nerve, including, for example, stimulation of molecularly-distinct vagus nerve afferents that are differentially expressed in the gut, lungs, heart, allergy, and stomach[29,30] to thereby selectively reduce or increase gastric pressure, alter motility, inhibit breathing or speed up breathing rates, etc. Additionally, embodiments of the invention can be employed to treat erectile dysfunction by injecting retrograde AAV prior to prostate surgery, thereby allowing for full nerve expression in case the nerve is cut during the surgery.

The methods and devices of the invention can control peripheral nerves situated under deep tissue structures with transdermal, optical signals and are of enormous benefit, integrating all of the advantages conferred by optogenetics while averting the drawbacks associated with implantable devices, such as mechanical failure, device tissue heating, and a chronic foreign body response.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 3A and 3B are perspective and side views, respectively, of a knee strap with a light source suitable for employing a method of the invention, as applied to a knee of a subject.

FIG. 15 is a plot of Monte Carlo ("MC") estimated normalized fluence rate as a function of distance from skin normalized to incident power for a 200 g rat.

FIG. 16 is an example of a biphasic EMG twitch waveform generated by the tibialis anterior (TA) muscle in response to transdermal illumination of the proximal tibia (160 mW laser power).

FIG. 17 is a representation of variation in transdermal (3, 5, 8 weeks) and direct-nerve (8 weeks) optical response as a function of dosage and age.

DETAILED DESCRIPTION OF THE INVENTION

Figure 1A:
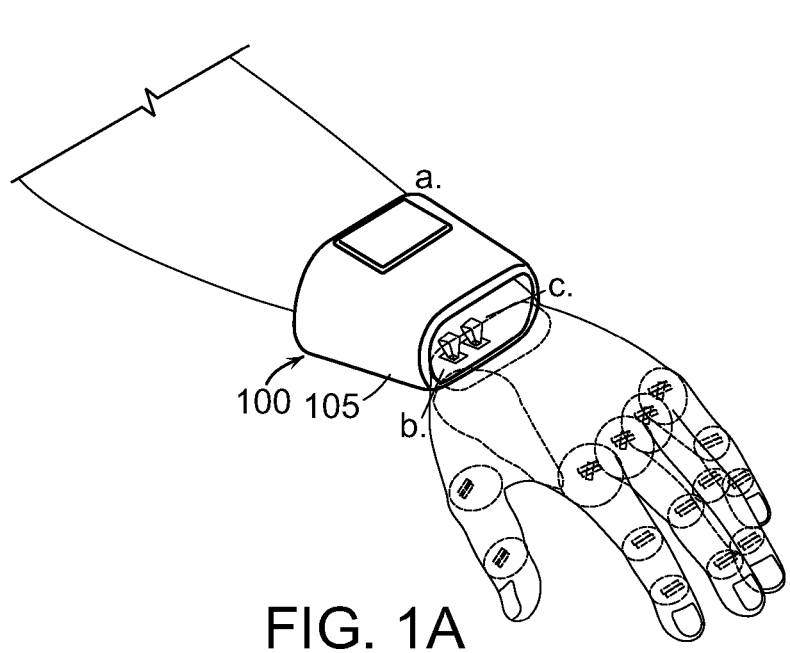
FIGS. 1A and 1B are perspective views of a wrist band light source employed in one embodiment of the invention.

The invention includes transdermal optogenetic peripheral nerve stimulation.

In one embodiment, the invention is a method of stimulating a nerve of a mammal, including the steps of optogenetically transforming a nerve in a mammal, wherein the nerve is susceptible to stimulation by selective application of transdermal light, and applying a light source to dermis of the mammal proximate to the optogenetically transduced nerve, thereby stimulating the nerve. In one embodiment the method further includes the step of actuating at least one sensor as a consequence of sensing at least one effect of the light source on the mammal by stimulation of the optogenetically transduced nerve, whereby the sensor generates a signal. In still another embodiment, the method further includes the step of processing the signal through a computational control element that, in response to the signal, provides a feedback control signal that modulates the light source and subsequent stimulation of the optogenetically transduced nerve.

In another embodiment, the invention is a method of optogenetically transfecting a mammal, including the step of administering to selected tissue of the mammal genetic material encoding light-sensitive opsins and a neural promoter, wherein genetic material causes a transdermal optogenetic peripheral nervous system response to light. In one such embodiment, the genetic material includes viral particles that operate as a viral vector to carry the genetic material. In a specific embodiment, the viral particles are adeno-associated viral (AAV) particles. In one embodiment, the adeno-associated viral particles can include at least one member selected from the group consisting of serotype 1, serotype 2, serotype 3, serotype 4, serotype 5, serotype 6, serotype 7, serotype 8, serotype 9, serotype 10 and serotype 11. In one particular embodiment, the viral vector is AAV6-hSyn-ChR2 (H134R)-EYFP. The genetic material can be administered at a value of at least $10^{14}$ copies of DNA per milliliter at an approximate injected volume scaled to the weight of the mammal. For example, the injected volume can be at least 10 µL per kilogram total animal weight of the mammal. In another embodiment, the genetic material is administered at a volume of at least $10^{11}$ copies of DNA per kilogram in a mammal. The viral vector can be administered, for example, by at least one method selected from the group consisting of intramuscular injection, sub-epineurial injection, and electroporation. In one embodiment, the tissue of the mammal to be transfected is within about 4 cm of a dermal surface of the mammal. In another embodiment, the light-sensitive opsin includes at least one member of the group consisting of ChR2(H134R), ReaChR, Chrimson, Chrimson Rs, Chrimson Cs, Chrimson R, CoCHR and JAWS. In another specific embodiment, the neural promoter includes at least one member of the group consisting of hSyn, CamKII, hThy-1UflaCAG, SST and hypocretin. In one embodiment of the invention, the tissue is at least one member of the group consisting of a nociceptive fiber, a motor neuron, a spindle fiber, a golgi tendon organ, a cutaneous fiber, a low threshold mechano-receptor (LTNR), a nerve stent, a common peroneal nerve, a vagus nerve, a cavernous nerve, a median nerve, an ulnar nerve, a radian nerve, a tibial nerve, a median plantar nerve, a sciatic nerve, a superficial peroneal nerve, a cavernosa nerve, a deep peroneal nerve, a sural nerve, a recurrent laryngeal nerve, and a musculocutaneous nerve.

In another embodiment, the invention is a wearable device for optogenetic motor control and restoring sensation in a mammal, including a wearable support, a power source at the wearable support, a controller at the wearable support and in electrical communication with the power source, and a transdermal light source coupled to the controller, the controller driving the light source to direct light from the wearable support and toward the mammal while wearing the support. In one specific embodiment, the wearable support is a strap. In a specific embodiment, the strap is a member selected consisting of a wrist strap, a knee strap, a necklace, a headband, an ankle strap, a leg strap, a stomach strap, and an arm strap. In another embodiment, the wearable support is an adhesive patch. In still another embodiment, the transdermal light source includes at least one member selected from the group consisting of a light emitting diode (LED), diode-pumped solid-state (DPSS) laser, a diode laser, a solid-state laser, a vertical-cavity surface emitting laser (VCSEL), and an edge emitting laser diode (EELD). In one embodiment, the light source is of a type that emits a wavelength in a range of between about 300 nm and about 1100 nm. In another embodiment, the wearable device includes at least one sensor in communication with the controller, whereby the at least one sensor provides sensory feedback to the controller which controls the light source to thereby selectively stimulate at least one optogenetically altered nerve. In one such embodiment, the sensory feedback is at least one member of the group consisting of cutaneous feedback and proprioceptive feedback. In a specific embodiment, the sensor is selected from the group consisting of an accelerometer, a position sensor, a torque sensor, and a gyroscope. In still another embodiment of the invention, the controller of the wearable device includes at least one member of the group consisting of a reflexive controller, a state-based controller and a pattern-recognition controller.

Using intramuscular or sub-epineurial injections of a viral vector or other DNA-mediated platform (such as electroporation) for transduction of genetic material into biological tissue, neurons in peripheral nerves can be transduced to functionally express an opsin along the entire length of the axon and its membrane. An opsin has the unique ability to enable the flow of ions in response to illumination with a specific wavelength of light. Sufficient ion flow leads to an action potential, which is an electrical signal that nerves use to control target tissue. The likelihood of an action potential depends on several variables including: 1) the density of opsin channels within the axon (driven by the concentration of injected particles, the total volume injected, the efficiency of transduction, and the diffusion of that genetic material), 2) properties inherent to the opsin itself including photocurrents and kinetics, and 3) optical variables including the power, shape, pulse train, and wavelength of light used to depolarize the axon. If the first two variables are optimized to provide high photocurrents and high opsin expression, it is theoretically possible to decrease the power of light required as described by the previously mentioned $3^{rd}$ variable. The optical sensitivity of nerves can be increased to such an extent as to allow for stimulation of nerves beneath the tissue surface with transdermal illumination. This adds a fourth anatomical variable to be considered, which comprises the distance between the nerve and the skin surface, the axon's relative position within the cross-section of the nerve, and the optical absorption and scattering properties of the tissues between the nerve and the skin.

In one embodiment, the invention includes injection of a specific adeno-associated virus (AAV) serotype 6 into a nerve or muscle in an amount sufficient to optogenetically transfect the target tissue. In a specific embodiment, the AAV6 virus containing the light-sensitive opsin ChR2 (H134R), a neuron-specific promoter (hSyn), and a tissue-marker (EYFP), and a high-concentration of viral particles (e.g. 1.0E14 vp/mL) was employed, as well as a method of repeated high-volume follow-up intramuscular and intra-nerve injections. As a result, opsin expression in the tissues was so strong as to enable nerve stimulation at low levels of incident light. Specifically, for nerves at a tissue depth of ~2 mm, muscle twitches were observed at an estimated nerve surface power of ~100 μW/mm². Despite the strong scattering properties of blue light in biological tissues, ~100 μW/mm² at 2 mm depth can be produced with incident light power at the surface of the skin of ~10 mW/mm², a rate which can be provided by a traditional low power laser pointer. Likewise, responses at up to 4 mm depth were produced with a higher incident power at the surface of the skin, up to ~160 mW/mm², such as can be provided by an LED array, demonstrating that wearable devices can control key aspects of human physiological function controlled by peripheral nerves without requiring any implants or even direct contact with skin.

There are several nerves, which are close enough to the skin to be appropriately targeted for transdermal peripheral nerve optogenetics. These include the nerves of the hand, leg, neck, and perineum. Some major nerve trunks, which run ~2 cm or less from the surface of the skin are listed in Table 1 below. Also shown are disease applications for the target nerve.

TABLE 1

| Nerve | Location | Innervates | Distance From Skin | Disease Application | Technology |
|---|---|---|---|---|---|
| Median N. | Wrist | Hand sensation and intrinsic muscles | 3.2 mm | Paralysis, amputation, pain | LED Wristband |
| Ulnar N. | Wrist | Hand sensation and intrinsic muscles | 2.1 mm | Paralysis, amputation, pain | LED Wristband |
| Radial N. | Elbow | Upper Limb Extensors | ~1 cm | Paralysis, amputation, pain | LED Elbow Brace |
| Common Peroneal N. | Knee | Foot Dorsiflexors | 8 mm-1 cm | Paralysis, foot-drop for stroke victims, pain | LED knee brace |
| Cavernosal N. | Perineum | Corpus Spongiosum | ~1 cm | Erectile Dysfunction | LED underwear |
| Vagus N. | Neck | Gut, Stomach, Heart, Lungs, Brain | ~1.7 cm | Obesity, Anorexia, IBD, Diabetes, Depression, Epilepsy | LED necklace |
| Tibial N. | Knee | Foot Plantarflexors and sensation | ~2 cm | Paralysis, amputation, pain | LED knee brace |

The method of the invention can be employed in many types of devices. For example, in one embodiment, the invention is a wearable device 100, 200 that is an illuminated wristband 105 or patch 205 for optogenetic motor control and sensation restoration in the hand, and includes a rechargeable battery and microcontroller, light source (e.g., LED) casing, a transdermal light, and an adhesive layer, as shown in FIGS. 1A, 1B, 2A and 2B, where "a" is a power source (e.g. battery), "b" is a light emitter (e.g. LED), "c" is a light (e.g., 470 nm), and "d" is an adhesive material (e.g., methacrylate). The wearable device 100, 200 includes a wearable support 105, 205, a power source "a" at the wearable support, a controller at the wearable support (e.g., integrated into the support) and in electrical communication with the power source, and a transdermal light source "b" coupled to the controller. The controller drives the light source to direct light "c" from the wearable support and toward the mammal while wearing the support.

Figure 1B:
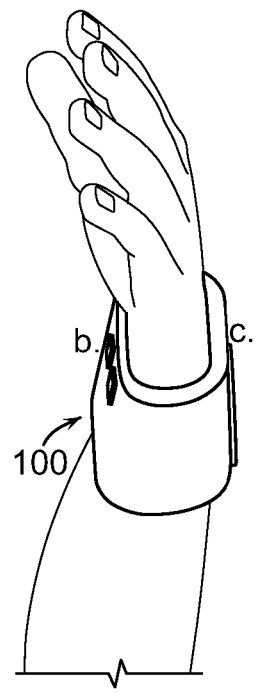
Figure 2A:
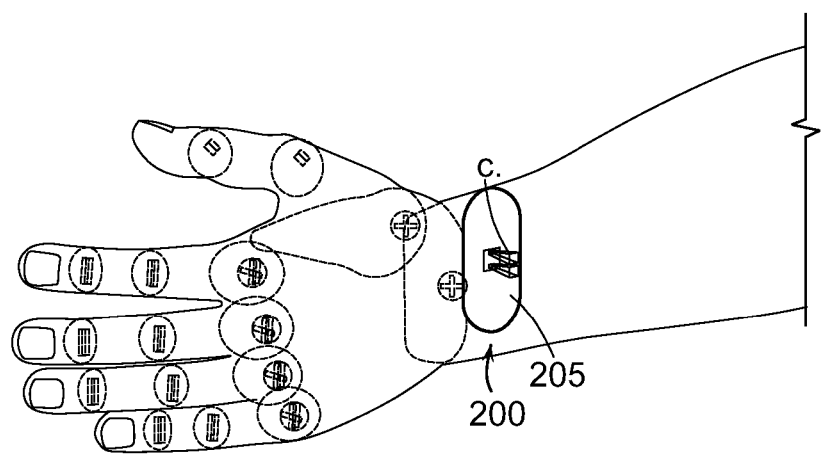
FIGS. 2A and 2B are perspective views of a light source adhering to a wrist of a subject, and suitable for use in the method of the invention.
Figure 2B:
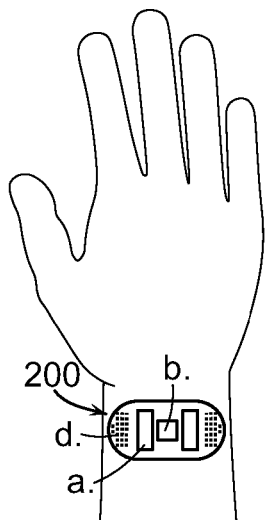

LEDs positioned in proximity to the median and ulnar nerves and a rechargeable battery may be encased in an ergonomic wristband. Although typically blue, the wavelength can be tailored to the wavelength required for the specific opsin injected. Depending on anatomy and power requirements, the device may or may not have a cooling system comprising a heatsink or fluid system to prevent burns at the surface. Microcontrollers inside the device may control the frequency, power, and duty cycle of the delivered light. Optogenetic stimulation of the median and ulnar nerves at the wrist (depicted here) provide fine motor control to intrinsic hand muscles including the lumbricals, the flexor pollicis brevis, the abductor pollicis, and others. In addition, targeted stimulation of sensory fibers could provide cutaneous or proprioceptive sensory feedback from touch sensors located on prosthetic fingers or hands. The form of the device can be either a wristband, as shown in FIGS. 1A and 1B, or an adhesive patch as shown in FIGS. 2A and 2B. A patch is affixed to the skin by a suitable biocompatible adhesive, such as is known in the art.

Figure 4A:
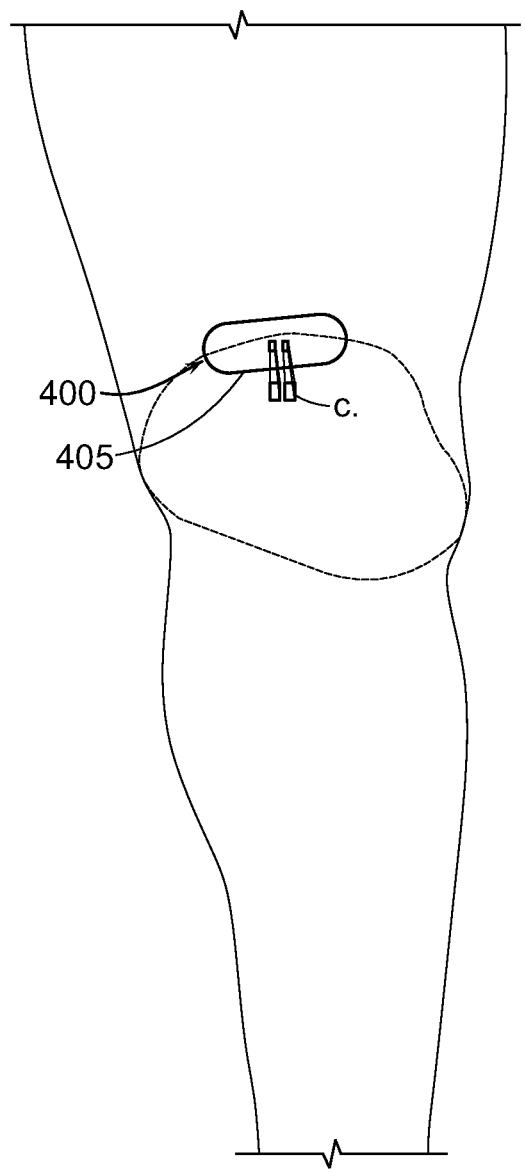
FIGS. 4A and 4B are perspective views of a light source adhering to skin near a knee of a subject, and suitable for use in the method of the invention.
Figure 4B:
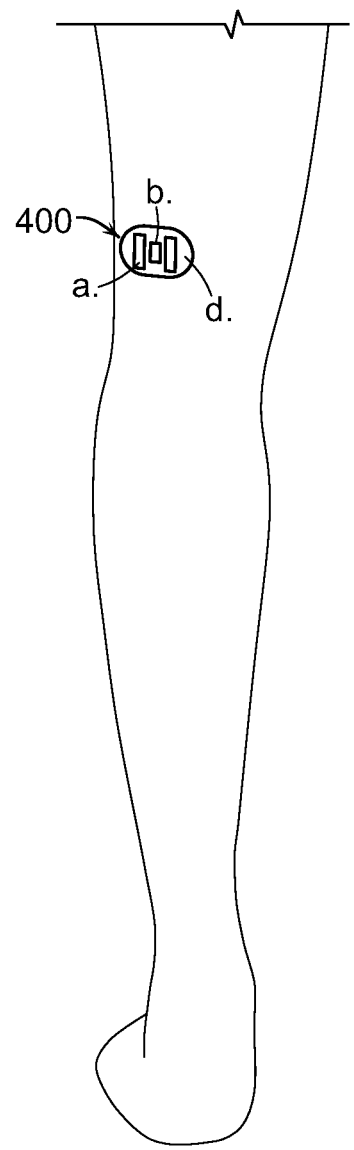

In another embodiment, the invention is an illuminated knee brace device 300 including wearable support 305, as shown in FIGS. 3A and 3B, or a patch device 400 including wearable support 405, as shown in FIGS. 4A and 4B, for optogenetic treatment of paralysis and foot-drop syndrome.

The letters "a," "b," "c," and "d," reference the same components indicated in FIGS. 1A, 1B, 2A and 2B. For example, LEDs positioned outside the common peroneal nerve as well as a rechargeable battery may be fitted to a knee brace. This allows the device to be secure while not restricting user motion. Although typically blue, the wavelength can be tailored to the specific opsin injected. Depending on anatomy and power requirements, the device 300, 400 may or may not have a cooling system comprising a heatsink or fluid system to prevent burns at the surface. Microcontrollers inside the device 300, 400 (e.g., integrated into support 305, 405) may control the frequency, power, and duty cycle of the delivered light. Optogenetic stimulation of the common peroneal nerve (depicted here) provides motor control over dorsiflexors in the foot. In foot-drop or paralysis, this technology causes muscles, including the tibialis anterior, extensor digitorum longus, and others, to fire based on sensors in the device that track the leg state including, but not limited to, accelerometers, position sensors, torque sensors, gyroscopes, etc. Optionally, suitable controllers, such as reflexive controllers, state-based controllers, or pattern-recognition controllers, can be employed. Also, other nerves can be employed by the method and wearable device of the invention such as the tibial nerve (not depicted), as well as its innervating muscles, although the tibial nerve lies about twice as deep as the peroneal nerve. In various embodiments, controllers can be used assist gait by firing at the proper time in paralysis. The design can take the form of a knee brace or a patch, for example. The knee brace itself, in various embodiments, can include an elastomer, fabric, silicone, or a suitable plastic material, such as with an exterior designed to remain aesthetically pleasing to the user. The patch embodiment of the wearable device of the invention can employ a suitable biocompatible adhesive, such as an acrylic or hydrocolloid. In one embodiment, there is a patch for each nerve, or a single patch with LEDs targeted to each nerve.

Figure 5A:
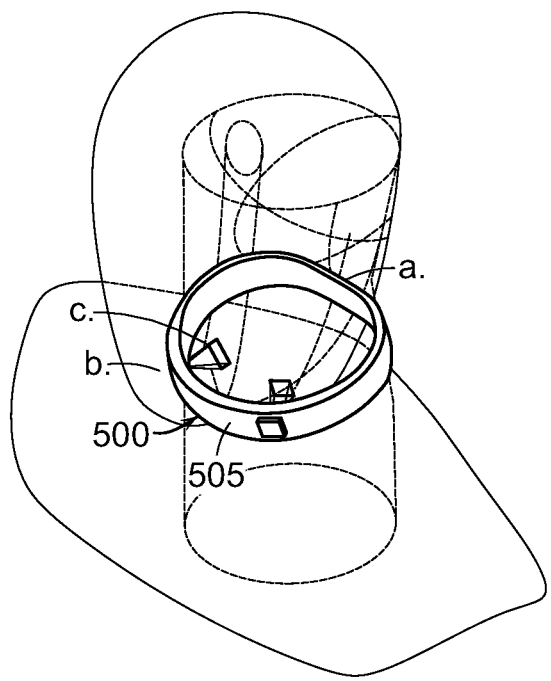
FIGS. 5A and 5B are perspective views of a neck strap with a light source suitable for use with another embodiment of a method of the invention.
Figure 5B:
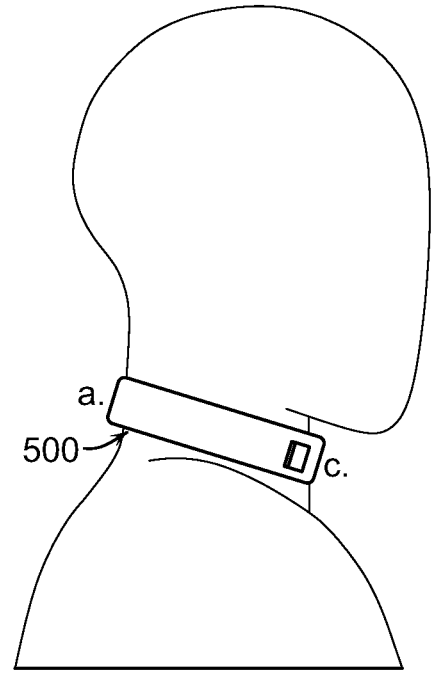
Figure 6A:
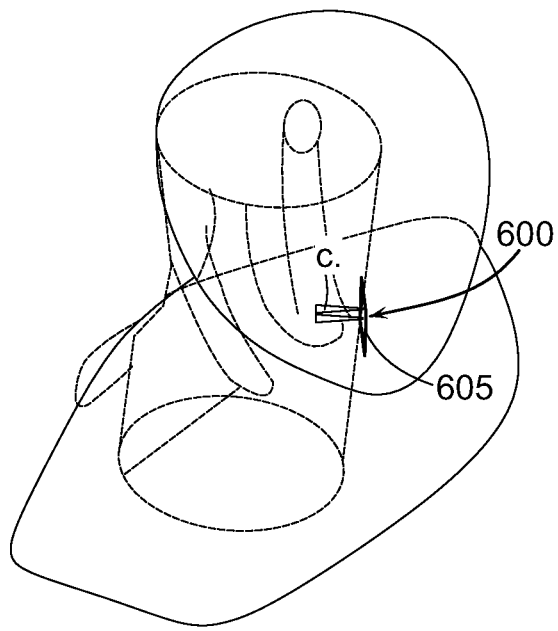
FIGS. 6A and 6B are perspective views of a light source adhering to a neck of a subject for use in still another embodiment of a method of the invention.
Figure 6B:
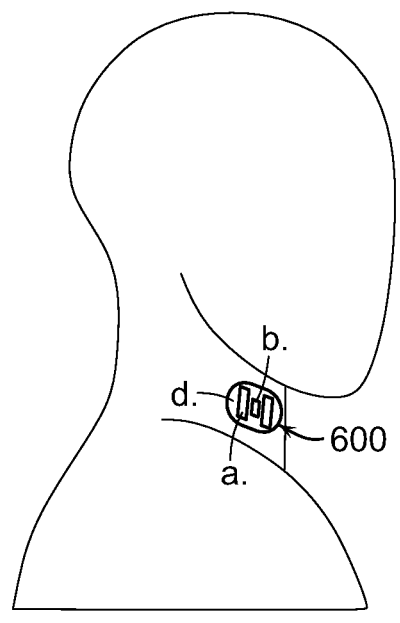

Still another embodiment of the wearable device of the invention is an illuminated necklace or patch for optogenetic treatment of vagus-implicated disorders. In one embodiment, LEDs and a rechargeable battery are encased within a necklace device 500 including wearable support 505, as illustrated in FIGS. 5A and 5B. The exterior may be designed to remain aesthetically pleasing to the user. This allows the device to be secure while not restricting user motion. Although typically blue, the wavelength can be tailored to the wavelength required for the specific opsin injected. Depending on anatomy and power requirements, the device may or may not have a cooling system comprising a heatsink or fluid system to prevent burns at a skin surface. Suitable microcontrollers, such as are known in the art, inside the device 500 variously control the frequency, power, and duty cycle of the delivered light. Optogenetic stimulation of the vagus nerve (represented in FIGS. 5A and 5B), for example, optionally provide autonomic control and sensation from its fibers in the gastrointestinal tract, heart, lungs, as well as treatment of mood and seizures through downstream neurological and endocrine pathways. The letters "a," "b," "c," and "d" correspond to the same items referenced in the previous drawings. This embodiment of the wearable device of the invention is employed, for example, to treat diseases defined by optogenetically targeting molecular-specific subtypes in the vagus nerve. The necklace or patch design can be customized to the individual. Suitable materials of construction of the necklace or patch include, for example, an elastomer, fabric, silicone, or plastic material. Another embodiment of a wearable device of the invention, shown in FIGS. 6A and 6B, is configured as a patch device 600 including wearable support 605 that is affixed to skin by a suitable biocompatible adhesive, such as an acrylic or hydrocolloid.

Figure 7:
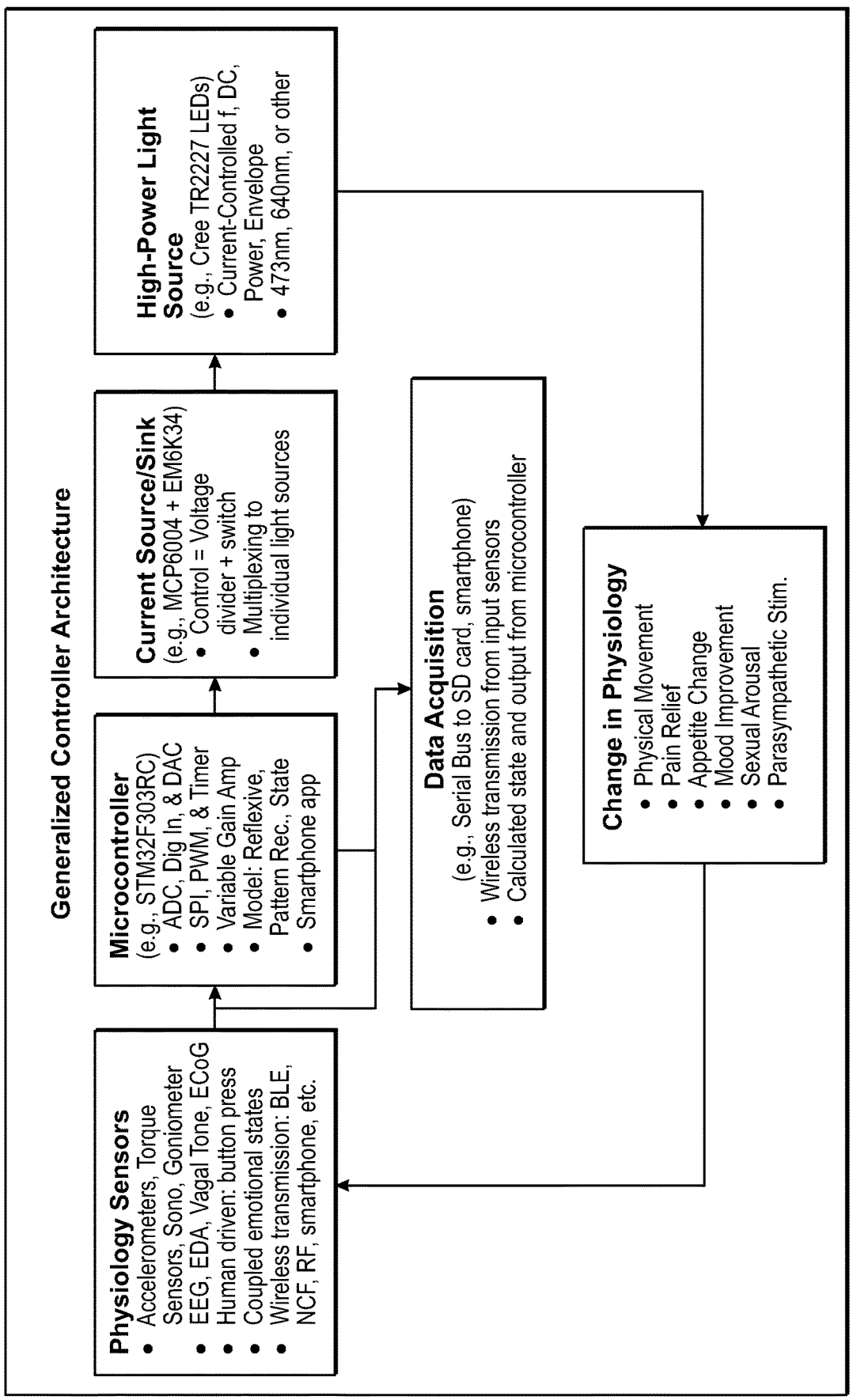
FIG. 7 is a representation of general architecture for closed-loop feedback control employing physiological sensors in one embodiment of the invention.

In still another embodiment, the invention includes a generalized control architecture for closed-loop transdermal optogenetic stimulation. In this embodiment, output physiology (e.g., position, velocity, pain, appetite, etc.) of a wearable device of the invention is modulated in a closed-loop fashion by a transdermal method of the invention. FIG. 7 is a schematic representation of a control diagram suitable for employment in methods and wearable devices (e.g., devices 100, 200, 300, 400, 500, 600) of the invention. As shown in FIG. 7, input sensors measure desired physiology, such as sweat, and movement sensors or neural signals, or a button press for manual control of a human emotional state as the closed-loop physiology change, along with wireless transmission capabilities. A microcontroller processes input signals from input sensors within a specific control strategy (such as defined above, and others that include, for example, reflexive, state-based or pattern recognition control) and output a desired signal (such as power, frequency, duty cycle, # LEDs) following data analysis of the input signals. A current source demultiplexes the input signal into individual currents for each light source channel. A light source, such as a high-powered LED or a DPSS laser, optimally emits light at a specific frequency through the skin to effect a change in output physiology, as described above, such as physical movement, pain relief, appetite change, mood improvement, sexual arousal, or others. The output of physiology sensors, and the model and line-output from the microcontroller, are for further processing or to be saved for model. The specific control architecture will be tailored for the specific application employed.

While FIG. 7 is a representation the general architecture for closed-loop feedback within one patient in one embodiment of the invention, patients may be coupled to one another, so that the input signal for one patient is driven by an output change in physiology from another patient. These can be linked by several technologies including Bluetooth (BT), Bluetooth Low Energy (BLE), Near Field (NFC), and Radiofrequency Communication (RF). Optionally, smartphones, as the processor and wireless communication device, can be employed both for a single individual, and coupling two or more individuals together. In this way, appetite control, for example, can be socially reinforced, so that when one person at a table is satiated, other individuals also begin to feel full. Alternatively, emotional states can be coupled so that when one individual feels compassionate as measured by certain sensors that can stimulate empathy in another individual.

Figure 8:
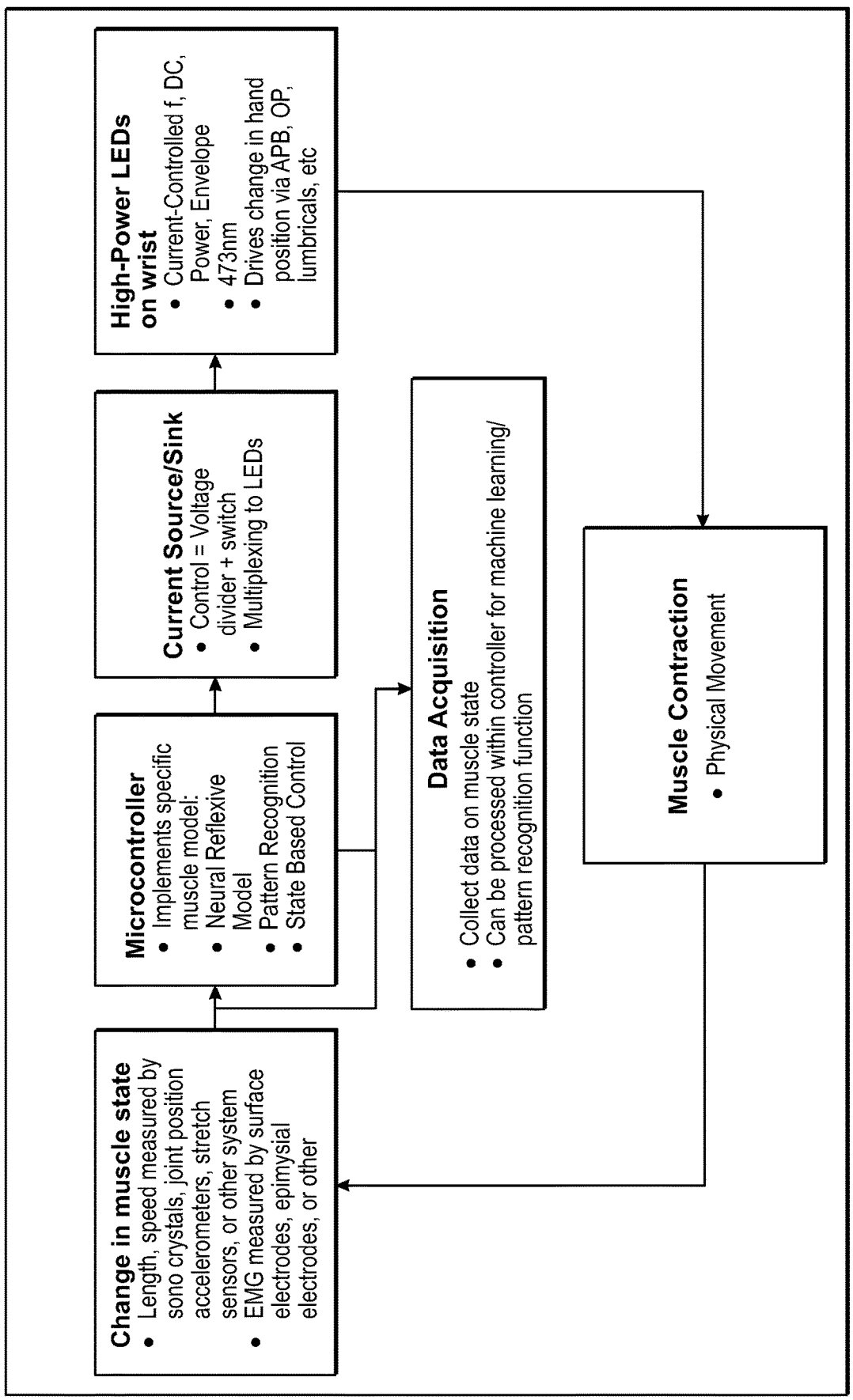
FIG. 8 is a schematic representation of a closed loop controller architecture suitable for use with the method and wearable device of the invention, and directed to motor control.

FIG. 8 is a schematic representation of a closed loop controller architecture suitable for use with the method and wearable device (e.g., device 100, 200) of the invention, and directed to motor control. In this figure, a change in muscle state as measured by certain physiological sensors including, but not limited to, electromyography electrodes, accelerometers, sono crystals, position sensors, and others, is used as the input to drive illumination of the optogenetically active nerve, which results in a physical movement owing to nerve-drive contraction of the muscle. This can be employed, for example, in restoration of fine motor control tasks in paralyzed individuals.

Figure 9:
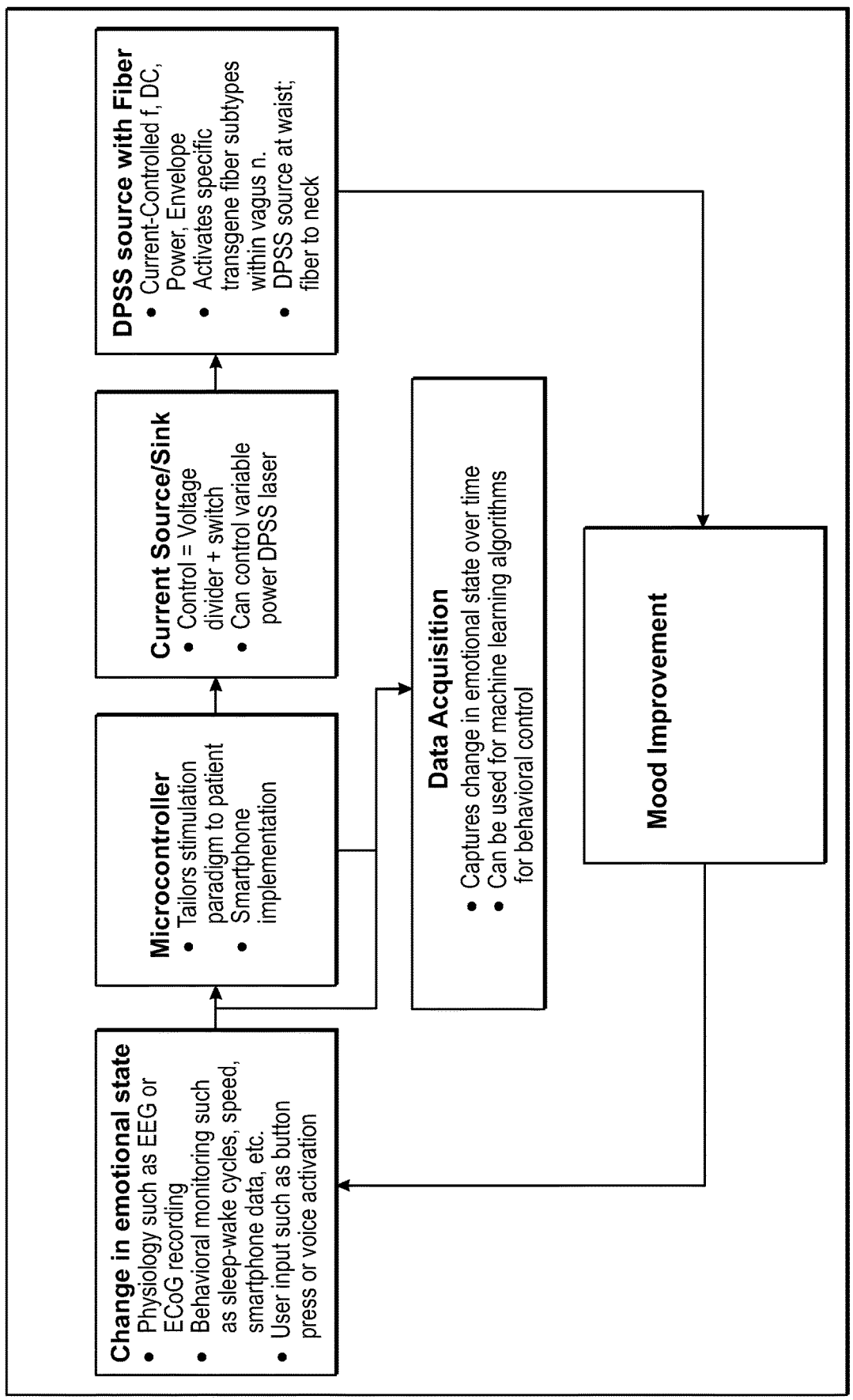
FIG. 9 is a schematic representation of a closed loop controller architecture suitable for use with the method and wearable device of the invention, and directed to treatment of depression.

FIG. 9 is a schematic representation of a closed loop controller architecture suitable for use with the method and wearable device (e.g., device 500, 600) of the invention, and directed to treatment of depression. In this diagram, mood is measured through certain physiology sensors that can include, but are not limited to, electroencephalography, electrocorticography, smartphone data based on user-device interactions, or direct user input. A microcontroller processes these data and uses them to provide input of certain temporal, frequency, amplitude, and phase characteristics to a light source located transdermal to the vagus nerve of an affected individual. Vagus nerve stimulation may result in an alleviation of symptoms and improve depressive behaviour symptoms, which in turn, will be tracked by the physiology sensors.

Figure 10:
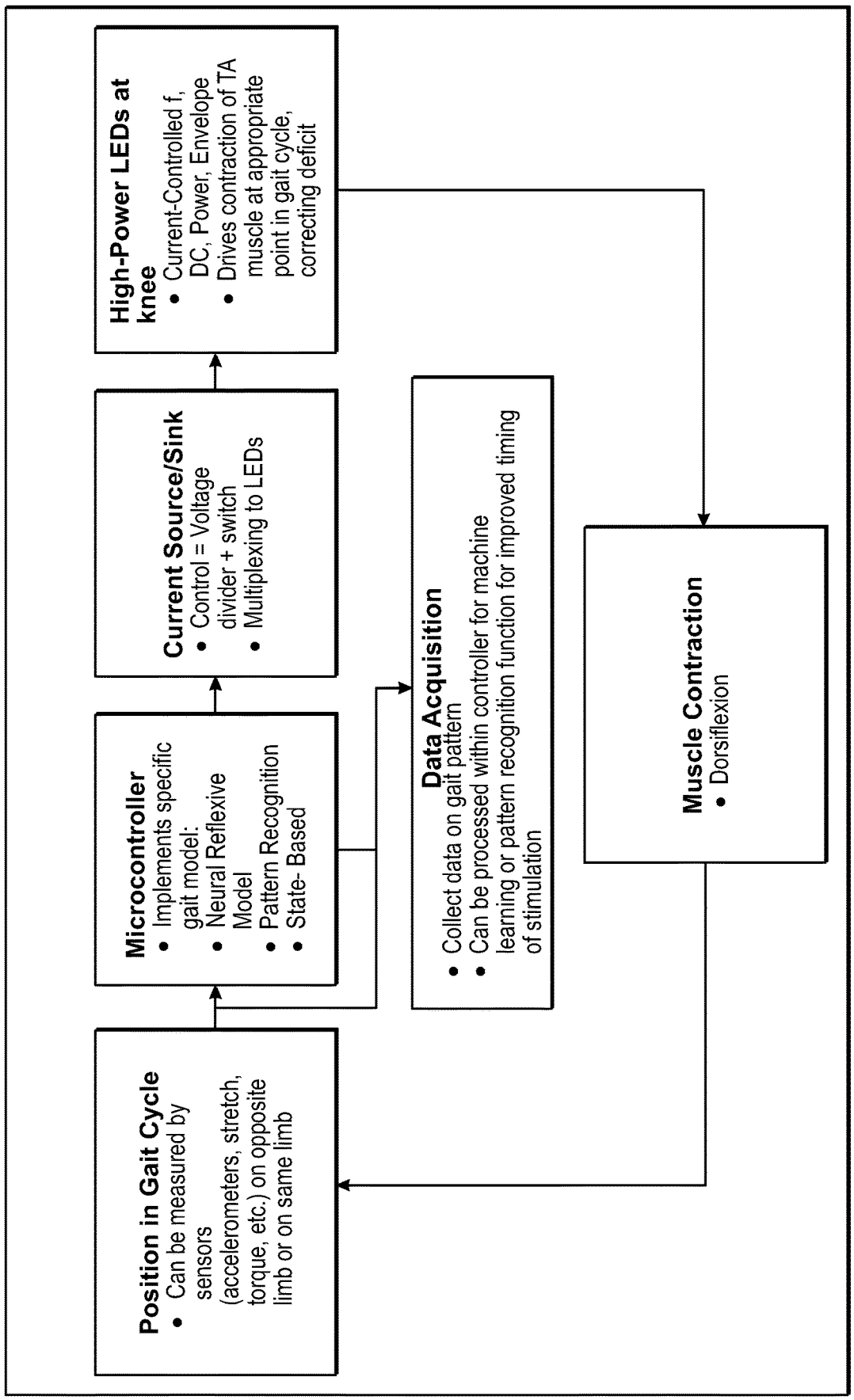
FIG. 10 is a schematic representation of a closed loop controller architecture suitable for use with the method and wearable device of the invention, and directed to treatment of foot drop.

FIG. 10 is a schematic representation of a closed loop controller architecture suitable for use with the method and wearable device (e.g., device 300, 400) of the invention, and directed to treatment of foot drop. In this diagram, position is measured during a gait cycle by employing sensors, such as accelerometers, stretch sensors, encoders, torque sensors or others on the same limb or on the opposite limb. These data are fed into a microcontroller, which employs an algorithm to interpret the appropriate position of the gait cycle. When the limb reaches the desired portion of the gait cycle to initiate stimulation, the microcontroller sends a signal to the current source which drives the light source required for optogenetic activation of the target nerve and downstream muscles. This results in a physical change (e.g., dorsiflexion in foot drop), which can restore an individual's functional gait. This change can be tracked in real-time through the closed-loop system to provide the appropriate physical state output required for optogenetically enhanced gait.

The following are representative examples of various embodiments of the invention.

EXEMPLIFICATION

Methods

All animal experiments were conducted on Fischer 344 rats under the supervision of the Committee on Animal Care at the Massachusetts Institute of Technology.

To measure the thickness and type of tissue between the skin surface and target nerve, a critical factor in determining how much light reaches the different nerve depths, the right hindlimbs of four 5-week old and four 8-week old Fischer 344 rats were extracted, postfixed for 48 hours in 4% paraformaledehyde (PFA), decalcified 36 hours in acetic acid, paraffin processed, embedded, sectioned at 25 µm thickness every ~250 µm, and stained with H&E. The sciatic nerve (s.n.) was traced to its division into the common peroneal nerve (c.p.n.) and tibial nerve (t.n.), which were followed distally, slice by slice, to their end plates at the tibialis anterior muscle (TA) and gastrocnemius muscle (GN), respectively. The c.p.n and t.n. depth, relative to skin, was measured on each slice; the slice with the minimum distance between nerve and skin surface was conservatively used for gathering the tissue geometry required for modeling. A Monte Carlo (MC) simulation was created for estimating fluence rate distribution in the rat c.p.n. and t.n. Key inputs to the model included tissue geometry, attenuation coefficients for scattering GO and absorption GO, and anisotropy factors in skin, muscle, connective tissue, epineurium and nerve, which were gathered from previous studies[15-18].

Figure 11:
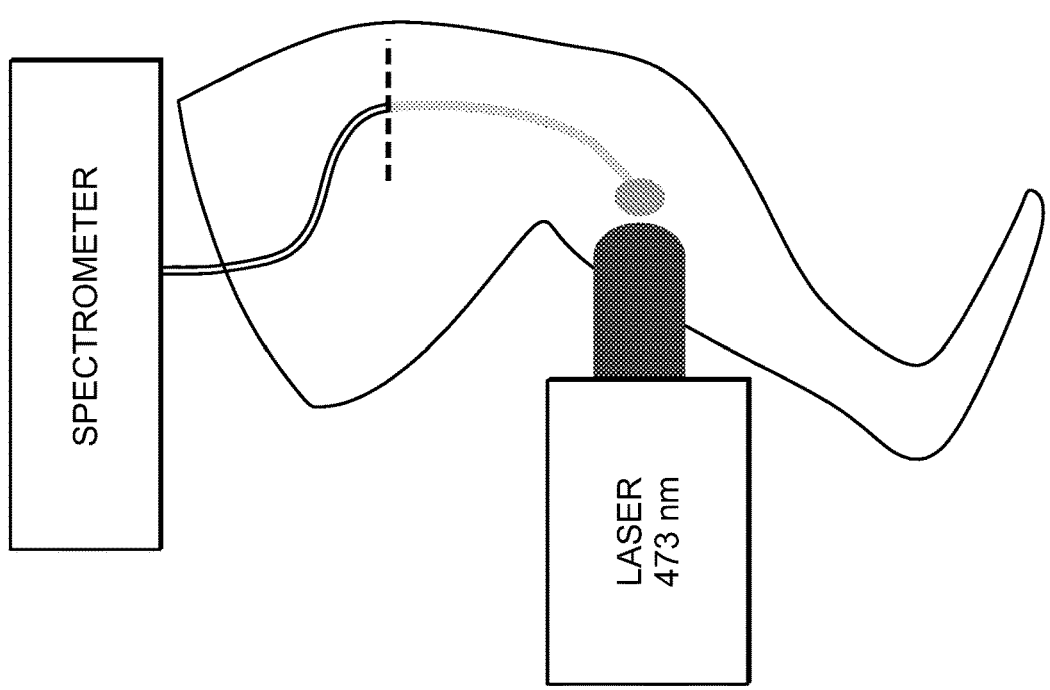
FIG. 11 is a schematic representation of direct fluence rate measurement.

To validate the fluence rate simulation and its applicability to other geometries, a direct measurement of fluence rate was pursued. A method previously used to measure fluence rate in a directionally isometric and minimally invasive manner involves a small ruby sphere directly coupled to a fiber-optic cable[19]. The measured intensity of the ruby's emission at its spectral peak of ~694 nm is directly dependent on fluence rate. The device was constructed by attaching a 400 µm diameter ruby sphere (Edmund Optics) to the polished edge of a multimode fiber optic cable with 400 µm core and 25 µm cladding (ThorLabs) with UV-curing epoxy (ThorLabs). The other end of the fiber optic cable was connected to a spectrometer (ThorLabs). The system was calibrated by illuminating the ruby sphere at known fluence rates with a DPSS 473 nm laser (OptoEngine) and measuring the spectrometer intensity at 694 nm. To measure direct fluence rate in vivo, a 5 mm skin incision was made at the lateral femur in two female, 200 g Fischer 344 rats. The isometric probe was inserted at the incision and routed distally into three separate regions of interest: 1) the subcutaneous space at the mid-tibia, 2) the c.p.n at its most superficial location, and 3) the t.n. at its most superficial location. Spectrometer intensity at 694 nm was measured with transdermal, 473 nm illumination for a range of powers, and translated to fluence rate using the calibration described above, and represented schematically in FIG. 11.

Viral vectors were produced in two batches enabling four dosages in five 8 week adult Fischer 344 rats (low, medium, high, and highest), and two dosages in ten neonate Fischer 344 rats (low and high). Low- and medium-dose AAV6-hSyn-ChR2(H134R)-EYFP viral vectors were produced from the Vector Core facility at the University of North Carolina Chapel Hill, provided in a concentrated dosage ($1.4 \times 10^{13}$ vp/mL). The hSyn promoter was employed to restrict optogenetic activation to nerve tissue, which was validated by directly illuminating the injected muscles and noting the lack of response. At the time of surgery, the thawed vector was diluted with 0.9% sterile saline to $2.8 \times 10^{12}$ vp/mL and $9.1 \times 10^{12}$ vp/mL for the low-dose and med-dose adult Fischer 344 rats respectively; the low-dose neonates were injected 2 days postpartum (P2) with $1.4 \times 10^{13}$ vg/mL virus as received. Ultra-high concentration AAV6-hSyn-ChR2(H134R)-EYFP viral vector was procured from Virovek Inc., at a titer of $1.2 \times 10^{14}$ vp/mL, and injected undiluted into the high- and highest-dose adult and high-dose P2 neonates. This high concentration (~$10^{14}$ vp/mL) enabled the high multiplicity of infection which resulted in the transdermal response. The injected volume was scaled to total animal weight at a volume of approximately 150 uL per kg weight during injection. Each animal showing transdermal expression therefore received at least $10^{11}$ viral copies of opsin DNA with the highest animals at 5E12 total viral particles (for a 150 g adult rat) or 1E12 total viral particles (for a 25 g neonate rat) which both equal roughly 3-5E13 viral copies per kg.

Fifteen rats (Charles River Laboratories) were housed under a 12:12 light:dark cycle in a temperature-controlled environment with food and water ad libitum. Under isoflurane anesthesia, a 1 cm skin incision was made over the tibia in the adults and the biceps femoris (BF) muscle was reflected from its proximal insertion at the tibia to reveal the c.p.n.'s synaptic junction at the TA end plate. 75 µL of virus was intramuscularly injected in 3 regions of TA muscle within 1 cm of the end plate at a speed of 5 µL/min with an additional 5 µL of virus directly injected into the c.p.n. at the end plate at a speed of 1 µL/min, totaling $1.8 \times 10^{14}$ vp and $7.3 \times 10^{11}$ vp for the low- and medium-dose adults respectively. For the high- and highest-dose adults, a total of 20 µL and 35 µL was injected at 5 µL/min into the TA with an additional 5 µL of virus injected at 1 µL/min directly into the c.p.n. at the end plate, totaling $3.0 \times 10^{12}$ vp and $4.8 \times 10^{12}$ vp respectively. In the five low-dose P2 neonate rats, 2 µL was injected through the skin into the TA at 1 µL/min totaling $2.8 \times 10^{10}$ vp. For the high-dose P2 neonate rats, 5 µL was injected through the skin into the TA at 1 µL/min; two weeks following, the right hindlimbs of the same animals were opened in the same method as the adults and 4 µL was injected directly into the TA at the c.p.n. endplate with an additional 1 µL into the nerve at 1 µL/min totaling $1.2 \times 10^{12}$ vp. Following all open injections, the BF was sutured with 5-0 vicryl, and the skin was closed with wound clips and tissue glue.

Figure 12:
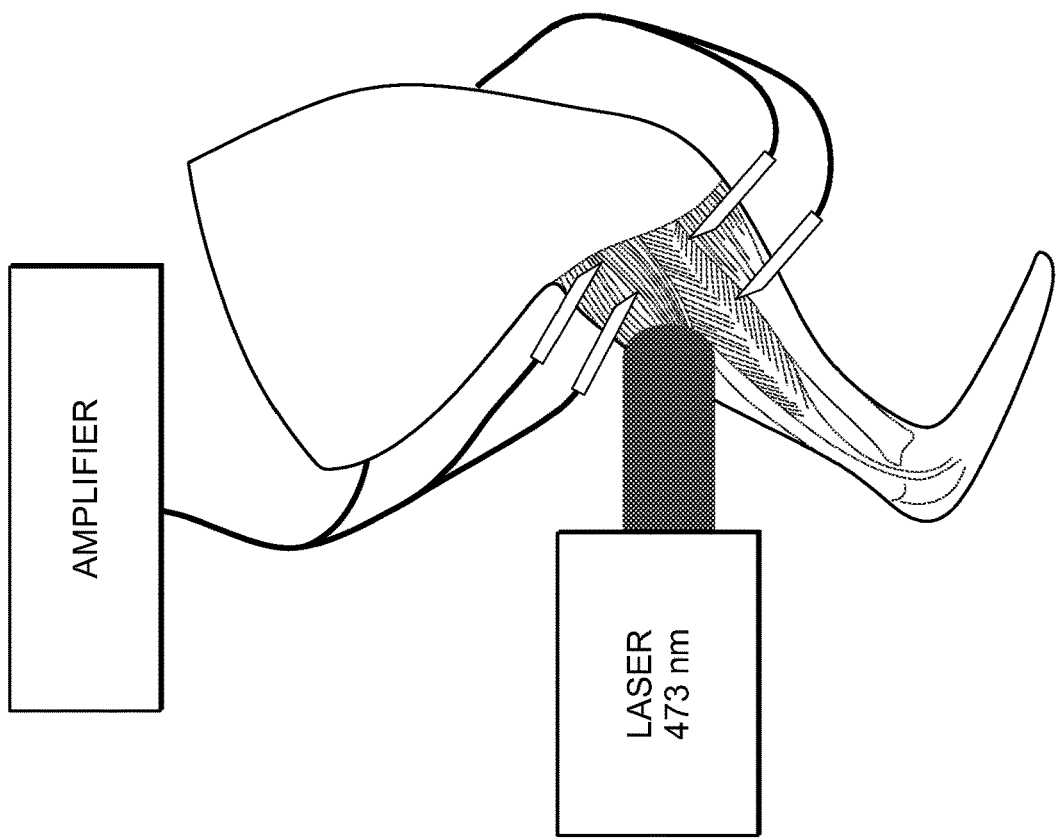
FIG. 12 is a schematic representation of transdermal optogenetic stimulation of a nerve with EMG recording in muscles according to one embodiment of the invention.

For each animal, a twitch response to 473 nm transdermal light was tested at 3, 5 and 8 weeks post-injection. At 8 weeks, direct optical stimulation of the nerve was also tested. To measure the strength of nerve responses, four 30 G monopolar electromyography (EMG) needles (Natus Medical) were directly inserted through the skin into the GN and TA for bipolar recording; a ground electrode was placed subcutaneously at the back. Careful needle placement limited acute inflammation at the illumination site. Needles were connected to a 20 kS/s multi-channel amplifier with a fixed 200× gain (IntanTech). A 473 nm laser (OptoEngine) was secured above the anesthetized animal to a stage assembly allowing for six degrees of freedom, as represented schematically in FIG. 12. The laser beam had a Gaussian cross-sectional profile and 3 mm diameter ($1/e^2$). Electrical signals controlling the laser parameters were simultaneously recorded by the amplifier, enabling temporal synchronization of laser pulses and EMG. Data analysis was performed in MATLAB software (The Mathworks, Inc.).

Following direct nerve illumination, rats were anesthetized and transcardially perfused with 4% PFA in PBS. Spinal cord, TA, and s.n. were dissected, post-fixed for 12 hours, paraffin processed, embedded, and sectioned at 10 μm. EYFP expression was amplified with Rb pAb anti-GFP (ab290, Abcam) at 1:200 (unless specified) with Alexa Fluor 568 (Fisher); s.n. was labeled with gt anti-CHAT (AB144P, Millipore) at 1:100 and Alexa Fluor 488 (Fisher), all in 1% w/v BSA in PBS-T. Immunofluorescence images were taken on an Evos FL Auto (Fisher) epifluorescence microscope at 10× and 20× and processed with ImageJ.

Results

Figure 13:
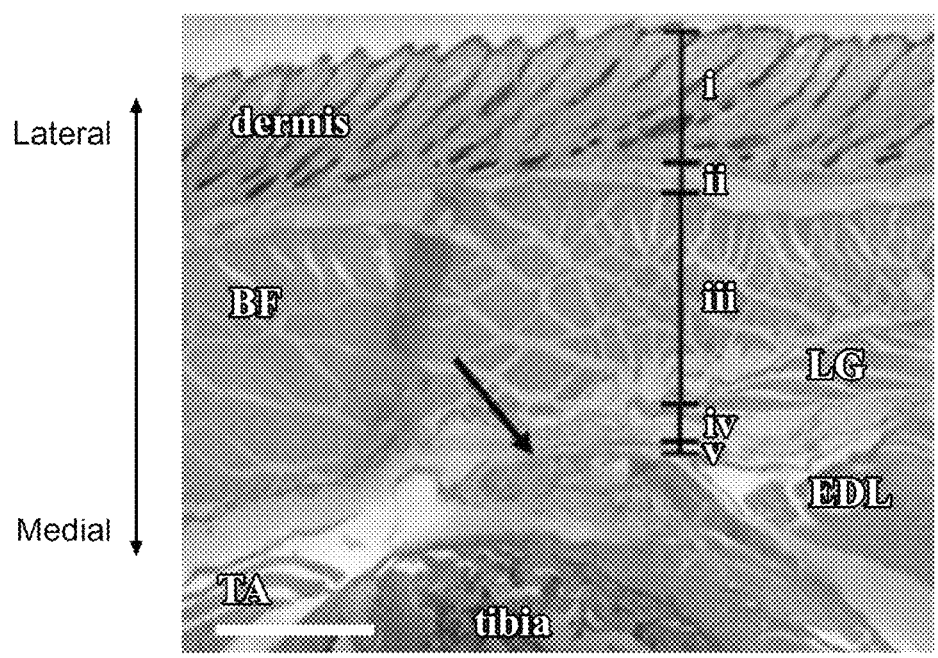
FIG. 13 is a Hematoxylin & Eosin ("H&E") cross-section to measure tissue depth in an 8-week female rat showing the peroneal nerve (p.n.) (arrow) adjacent to proximal tibia at most superficial location of the nerve with i. skin, ii. connective tissue, iii. muscle, iv. connective tissue, v. epineurium (BF=biceps femoris, LG=Lateral Gastrocnemius (GN), EDL=Extensor Digitorum Longus): scale bar 1 mm.
Figure 14:
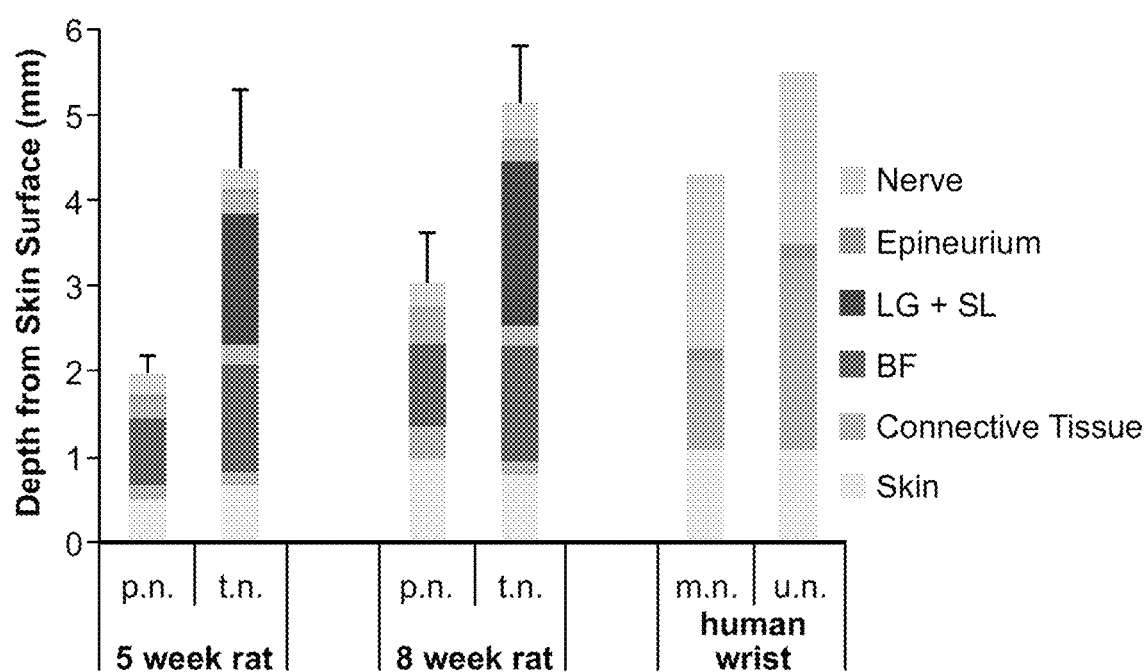
FIG. 14 are representations of common peroneal nerve (c.p.n.) and tibial nerve (t.n.) depths by tissue type by rat age compared to human median nerve (m.n.) and ulnar nerve (u.n.) depths at adult wrist.

The measured tissues between the skin surface and nerve comprised skin, connective tissue, muscle, and epineurium (FIG. 13), with total depth ranging from 1.4 mm for the c.p.n. in the 5-week rat to 5.3 mm for the t.n. in the 8-week rat (FIG. 14). For human comparison, the distance from skin surface to the median and ulnar nerves at the wrist measure 2.1 mm and 3.2 mm respectively[20] (FIG. 14). For a 200 g rat, the fluence rate along the centerline below the incident laser as a function of distance shows ~2 orders of magnitude and ~3.5 orders of magnitude declines for the c.p.n. and the t.n. respectively, as shown in FIG. 15.

Direct fluence rate measurements are shown alongside the MC simulation results in Table 2, showing good agreement with a maximum deviation of 12%. Table 2 shows the normalized fluence rate for 5-week and 8-week rats at the c.p.n. and t.n., as well as for the median nerve and ulnar nerve of a human wrist.

TABLE 2

| Fluence Rate ($1/mm^2$): Normalized to Incident Power | | | |
|---|---|---|---|
| | Subcutaneous | Peroneal N. | Tibial N. |
| Direct Measure | $1.9 \times 10^{-2} \pm 0.2 \times 10^{-2}$ | $3.9 \times 10^{-3} \pm 1.0 \times 10^{-2}$ | $6.3 \times 10^{-5} \pm 1.2 \times 10^{-5}$ |
| MC Simulation | $2.1 \times 10^{-2}$ | $4.0 \times 10^{-3}$ | $5.9 \times 10^{-5}$ |

As shown therein, the normalized fluence rate was found to be $3.9 \times 10^{-3}$ mm$^{-2}$ at the peroneal nerve for the 8-week rat and $1.1 \times 10^{-3}$ mm$^{-2}$ at the tibial nerve of a 5-week old rat, as can be seen in Table 3.

TABLE 3

| Fluence Rate ($1/mm^2$): Normalized to Incident Power | | |
|---|---|---|
| | Peroneal N. | Tibial N |
| 5 week (~80 g) | $8.9 \times 10^{-3}$ | $1.1 \times 10^{-3}$ |
| 8 week (~135 g) | $4.2 \times 10^{-3}$ | $6.3 \times 10^{-4}$ |
| | Median N. | Ulnar N. |
| Human wrist | $1.9 \times 10^{-2}$ | $6.2 \times 10^{-3}$ |

As such, a 160 mW, 473 nm laser source, transdermally incident, would yield fluence rates of 624 μW/mm$^2$ and 176 μW/mm$^2$ at each of the respective nerves. These values are below the previously published optical threshold for ChR2 (H134R) activation in peripheral axons, although cultured neurons have seen activations in this range[21]. The estimates for normalized fluence rate at the surface of the median nerve and ulnar nerve in the human wrist show comparable magnitudes to the rat, with 160 mW incident light providing 3 mW/mm$^2$ and 992 μW/mm$^2$ respectively.

Figure 18:
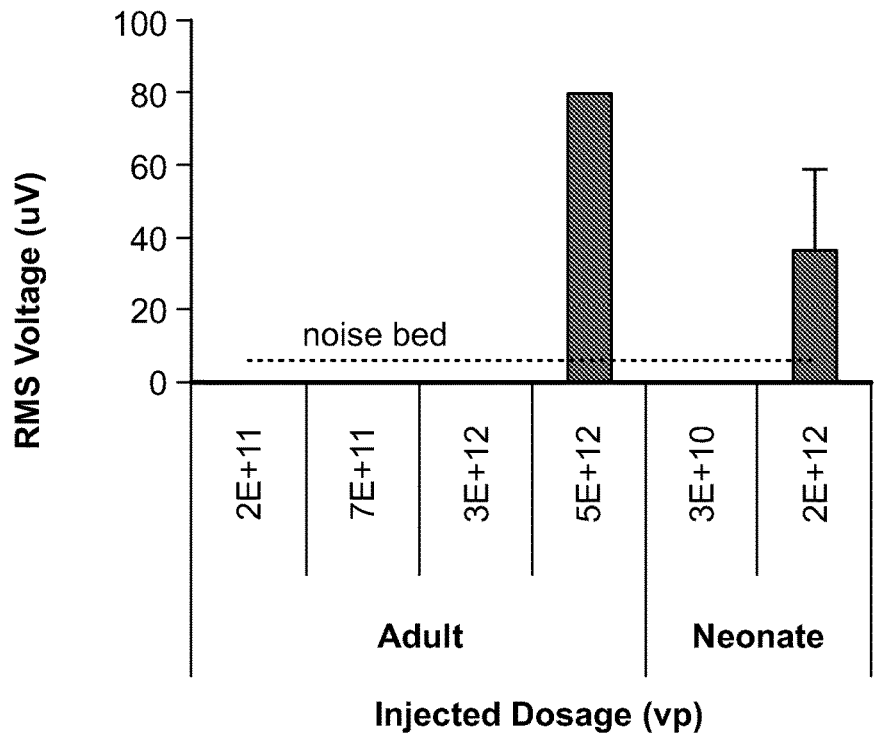
FIG. 18 is a representation of calculated RMS EMG voltage in TA at 5 weeks post-injection for 5 s transdermal stimulation: n=2 (1 Hz, 15 ms pulse width (PW), 160 mW skin surface power).

The presence of transdermal optical stimulation was defined by repeatable, temporally synchronized EMG twitches of characteristic triphasic or biphasic pattern, as shown in FIG. 16. Transdermal illumination produced twitches in 7 of the 15 tested animals at 5 weeks post-injection, with an 8$^{th}$ responding at 8 weeks post-injection, as shown in FIG. 17. There appeared to be a relationship between dose and the likelihood of transdermal stimulation in both adults and neonates, as indicated in FIG. 18. However, the stability of the transdermal response was uncertain. At 8 weeks post-injection, ⅗ of the P2 neonates and ½ of the highest dose adults previously showing a transdermal response lost the response. These nerves remained optogenetically excitable with direct nerve illumination.

Figure 19:
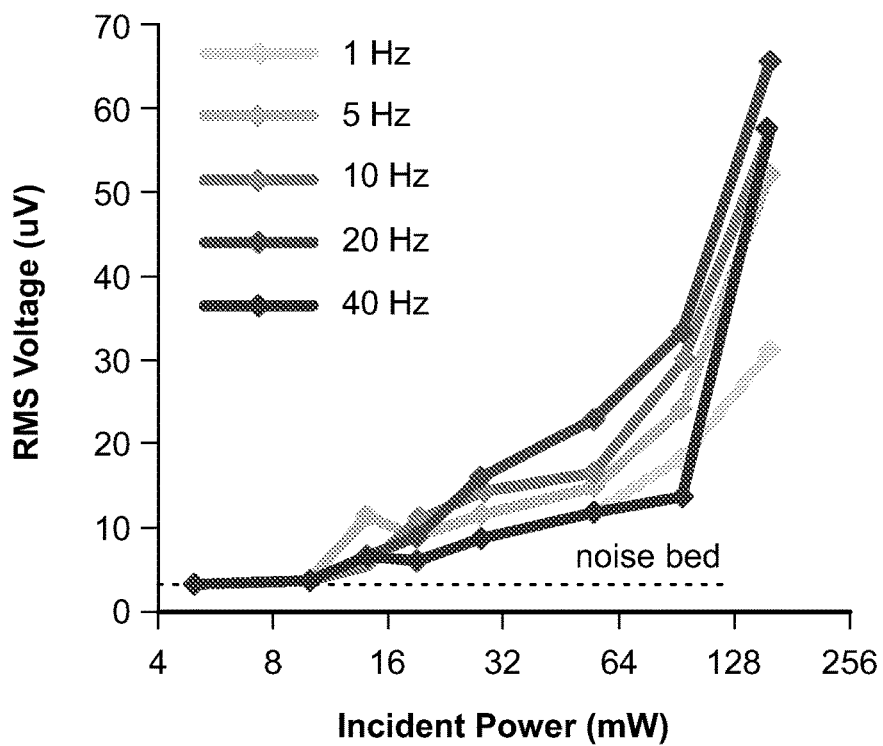
FIG. 19 is a representation of calculated RMS EMG voltage in TA as a function of incident power and frequency for 5 s transdermal stimulation for P2 neonate at 5 weeks post-injection: n=1 (10 ms PW).
Figure 20:
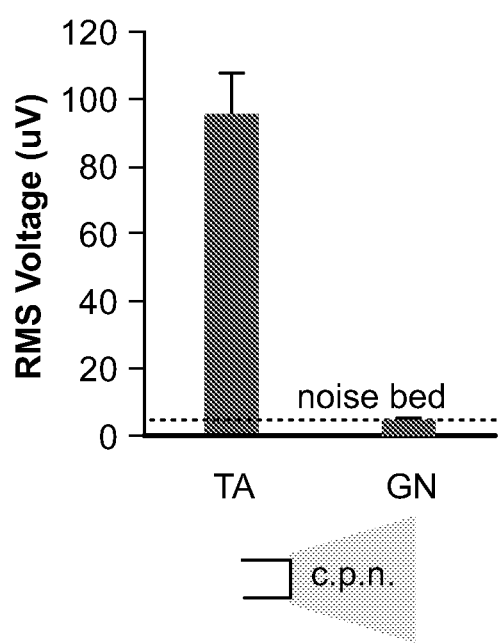
FIG. 20 is a representation of RMS voltage showing selective stimulation of TA without GN in response to illumination at proximal tibia: n=2 (1 Hz, 10 ms PW, 160 mW skin surface power).
Figure 21:
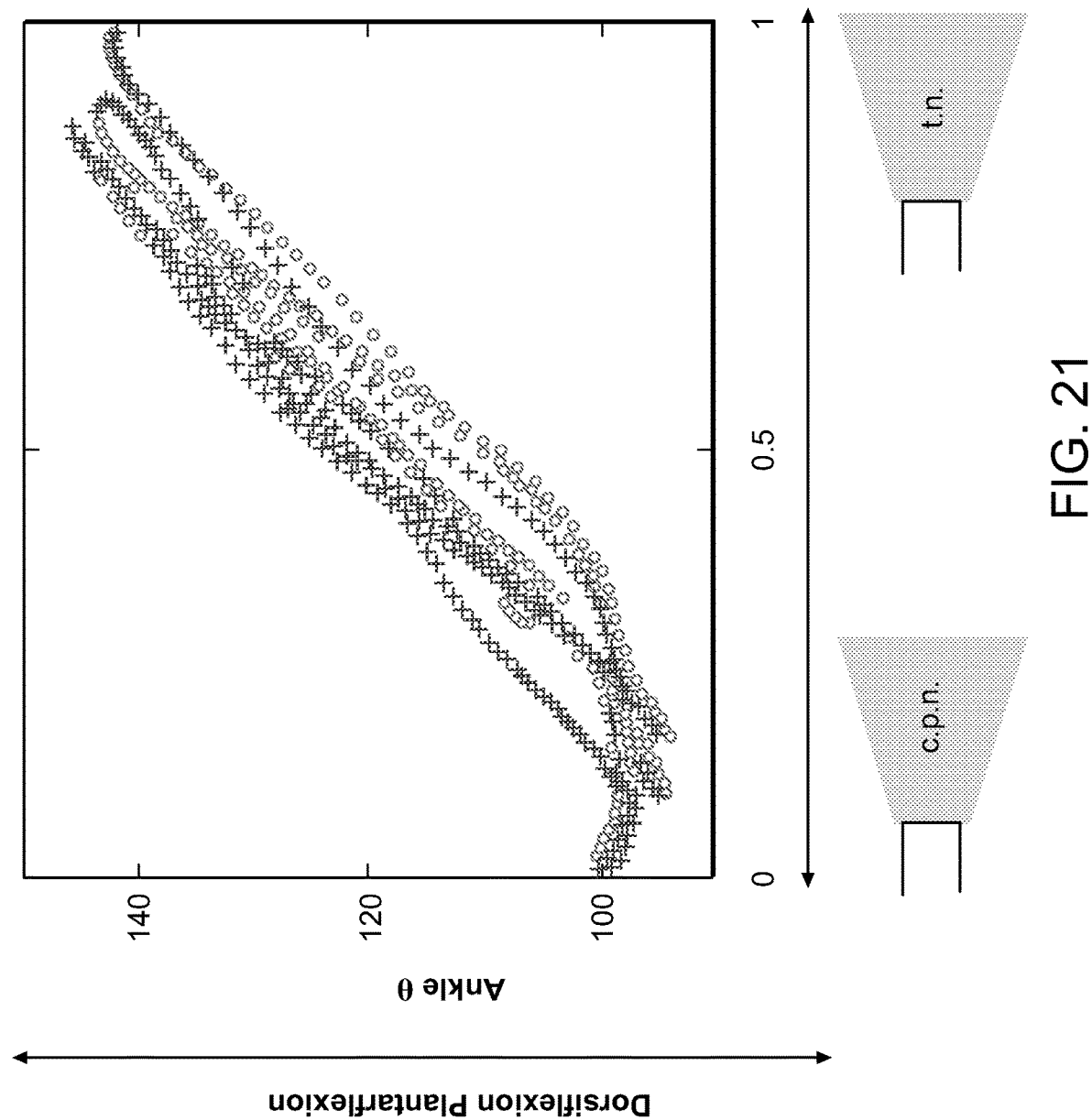
FIG. 21 is a plot of ankle angle as a function of light position as a laser was moved between proximal tibia and mid-calf corresponding to c.p.n and t.n., respectively, and wherein the horizontal axis normalized over ~8 mm distance between illumination regions; position data smoothed with 30 point moving average filter: n=1.
Figure 22:
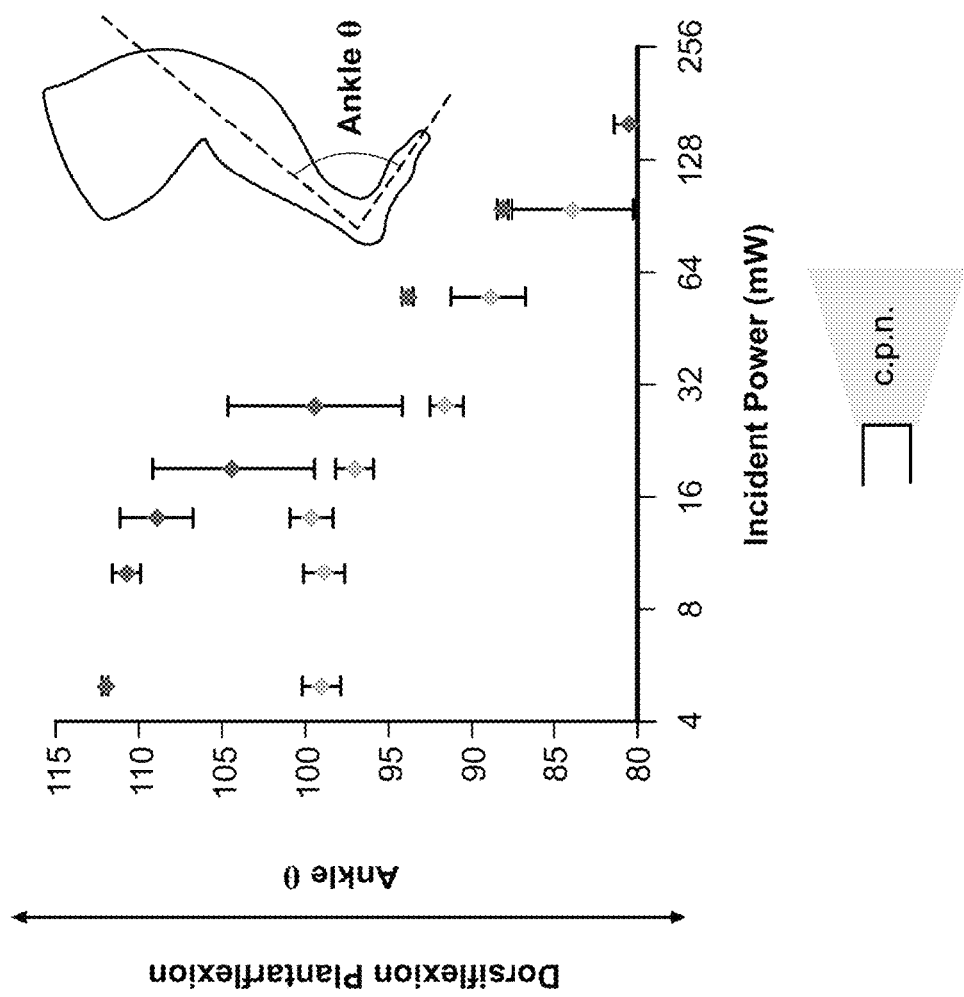
FIG. 22 is a representation of ankle angle as laser power at a proximal tibia is ramped up from 5 mW to 160 mW (violet) and back down to 5 mW (blue): n=2.

The transdermal RMS voltage was found to increase as a function of laser power; twitch responses were seen with as low as 10 mW incident power, which corresponds to a Monte Carlo (MC) simulated fluence rate at the surface of the nerve of 89 μW/mm$^2$, as shown in FIG. 19. In addition, it was found that the transdermal response could target muscles highly specific to laser position on the skin surface, as shown in FIG. 20. Illumination of the skin at the proximal tibia, superficial to the insertion of the p.n. in the TA, resulted in dorsiflexion and stimulation at mid-calf, superficial to the insertion of the t.n. in the GN, resulted in plantarflexion, as can be seen in FIG. 21. Alternating laser position could accurately produce a desired ankle position with little hysteresis or fatigue. In addition, incident power could be modulated to affect ankle position—with the laser targeting the skin superficial to the c.p.n. ramped from 10 mW to 160 mW, the ankle slowly dorsiflexed. A subsequent decrease in power resulted in the return to plantarflexion, although baseline not achieved, likely due to resting tension, as shown in FIG. 22.

Figure 23:
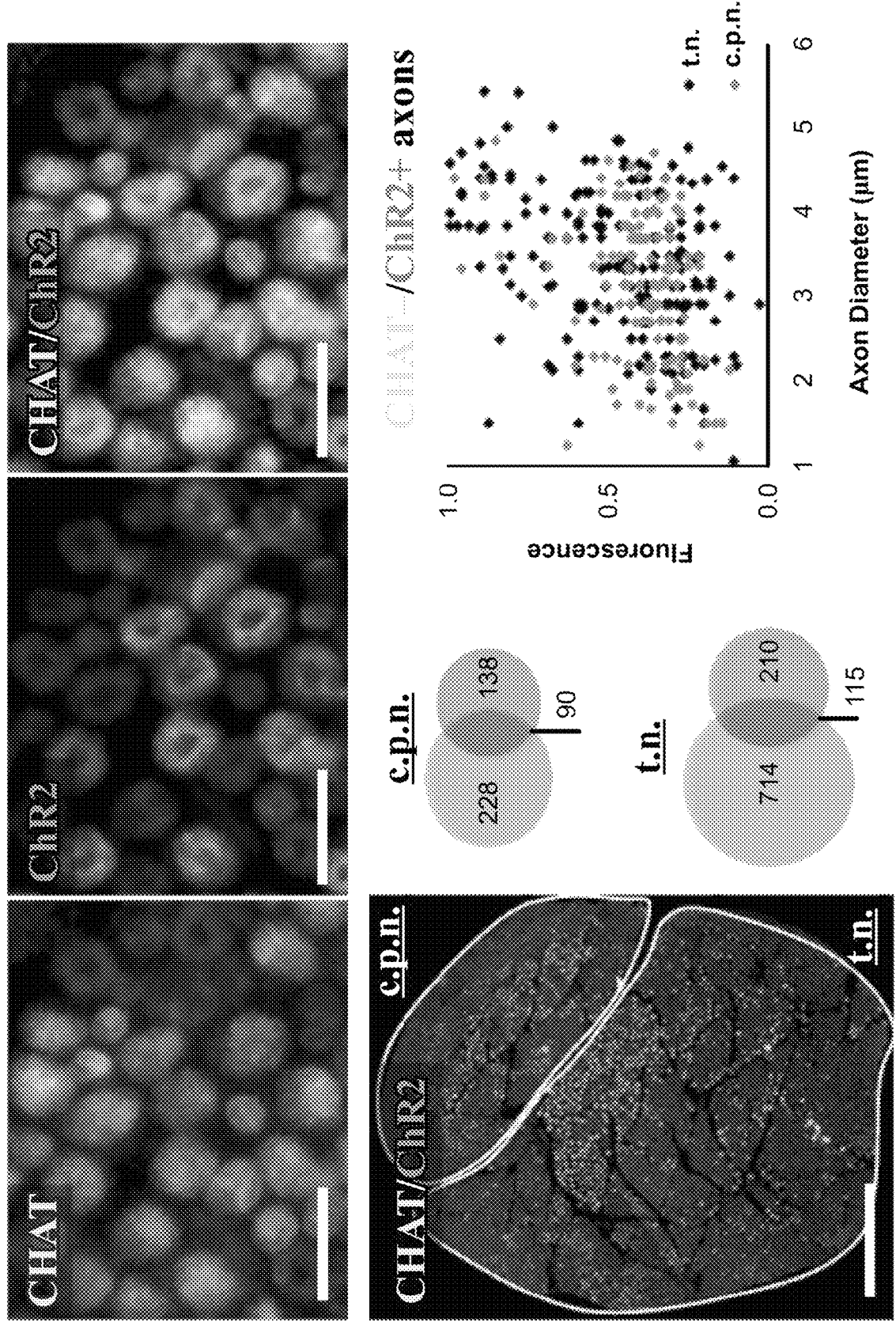
FIG. 23 are photographs and representations of P2 neonate sciatic nerve (s.n.) labeled for CHAT (green) and ChR2 (red) with corresponding counts in both the c.p.n. (targeted) and t.n. (non-targeted): scale bar 12.5 µm (top) and 150 µm (bottom).
Figure 24:
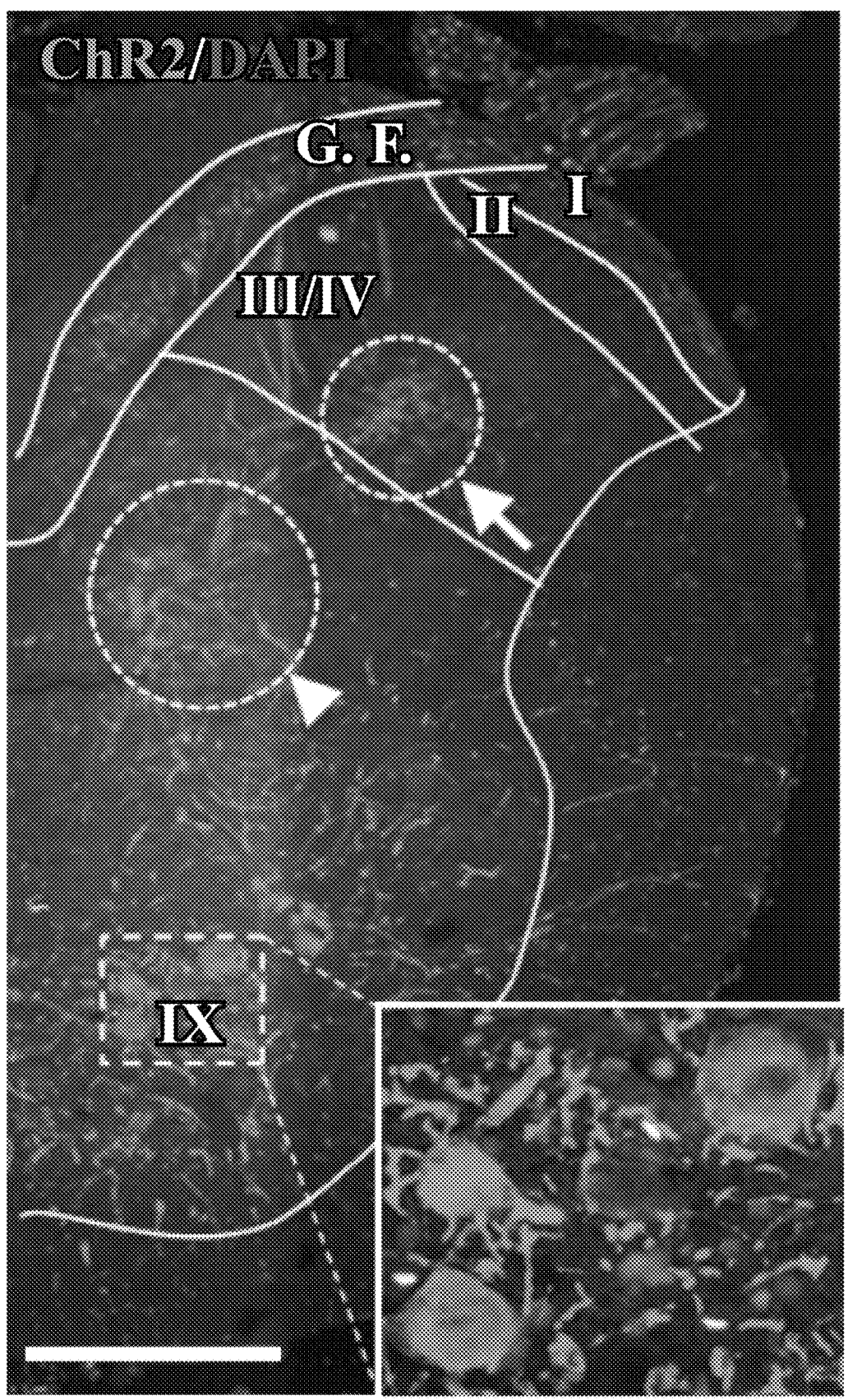
FIG. 24 is an annotated photograph of a half-section of right spinal cord of P2 neonate between L3-S1 labeled for ChR2 (red) and DAPI (blue). Within white matter, laminae I-IV & IX are outlined and likely nucleus proprius (arrow) and dorsal nucleus of Clarke (arrowhead). Within grey matter, gracile fasciculus (G.F.) outlined: scale bar 325 µm.

Evaluation of s.n. cross-sections showed strong ChR2+ fluorescence in both c.p.n and t.n. divisions, as represented in FIG. 23. Non-targeted t.n. shows strongest ChR2+ expression in the fascicles directly adjacent to the c.p.n, possibly indicating perineurial crossing of AAV at the level of the s.n. during retrograde transport. Despite the goal of exclusive motor fiber transfection, only 40% and 35% of c.p.n. and t.n. ChR2+ axons co-express CHAT, a marker of motor neurons[22]. Fluorescence and diameter were measured for each ChR2+/CHAT- fiber to identify if the sensory fibers exclusively comprised the large diameter muscle spindle fibers, but no strong relationship between fluorescence and diameter was found. Histological cross-sections of the spinal cord show strongest expression within the several bright ChR2-eYFP+ motor neurons in the ventral horn of the high-dosed animal (FIG. 24). Sensory fiber transfection is also seen in spinal cord sections with ChR2+ dorsal horn expression appearing strongest in the nucleus proprius, dorsal nucleus of Clarke, and first order fibers of the ipsilateral gracile fasciculus, all of which indicate proprioceptive and touch sensors from the lower limbs (FIG. 24). Faint ChR2+ expression is seen in lamina I of the dorsal horn, indicating few ChR2+ Aδ or C fibers, possibly consistent with a protective "foot-tucking" response seen during transdermal foot stimulation of the awake, freely-moving rat.

Figure 25:
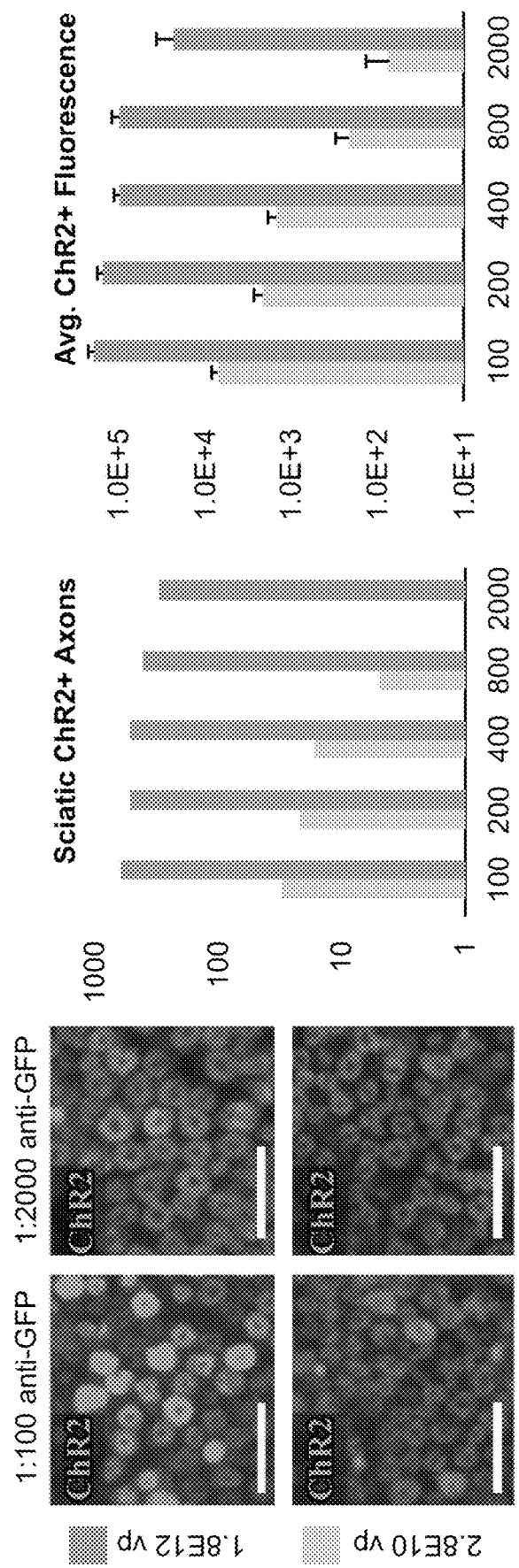
FIG. 25 are photographs and histographs illustrating serial dilution of anti-GFP primary antibody to evaluate relative opsin density between low-dose and high-dose P2 injections, with 1:100 and 1:2000 dilutions shown: scale bar 17.5 µm; comparison of transduction efficiency vs. primary antibody concentration shown in both total axon count and summed fluorescence of all ChR2+ axons for both doses.

To compare relative opsin density between dosages, both ChR2+ axon counts and summed average fluorescence was measured within the s.n. for several concentrations of primary antibody, as represented in FIG. 25. The serial dilution shows an order of magnitude difference between high-dose and low-dose rats in both axon counts and total fluorescence. This difference increases to ~2 orders of magnitude for the axons and ~3 orders of magnitude for the fluorescence as the concentration of primary in blocking solution decreases from 1:100 to 1:800. The relative drop in fluorescence as antibody concentration decreases suggests a weaker density of opsin channels within ChR2+ axons in the low-dose animal, due to non-specific binding out-competing the few ChR2+ antigen sites present within the axons. This histological evidence suggests a higher average opsin channel density per axon in the high-dose animal, providing a mechanistic rationale for the lower fluence required at the axon surface for transdermal stimulation in the high-dose rats.

DISCUSSION

Transdermal illumination of peripheral nerve targets could be achieved by utilizing ultra-high virus concentration to inject more viral particles and therefore more transgene copies in the motor neuron genome, translating to a higher density of ChR2 channels in the axon, and a lower fluence rate required for depolarization. The fluence rates at the surface of the nerve (89 $\mu W/mm^2$ and 176 $\mu W/mm^2$ for the 5-week c.p.n. at 10 mW and t.n. at 160 mW laser power respectively) are both roughly an order of magnitude lower than previously published data on light delivery required for ChR2(H134R) activation, indicating that increasing the total number of AAV particles delivered can improve the sensitivity of optogenetically active axons to illumination.

REFERENCES

1. Iyer, S. M. et al. Virally mediated optogenetic excitation and inhibition of pain in freely moving nontransgenic mice. *Nat. Biotechnol.* 32, 274-8 (2014).
2. Llewellyn, M. E., Thompson, K. R., Deisseroth, K. & Delp, S. L. Orderly recruitment of motor units under optical control in vivo. *Nat. Med.* 16, 1161-1165 (2010).
3. Ye, H., Daoud-El Baba, M., Peng, R.-W. & Fussenegger, M. A synthetic optogenetic transcription device enhances blood-glucose homeostasis in mice. *Science* 332, 1565-1568 (2011).
4. Bickel, C. S., Gregory, C. M. & Dean, J. C. Motor unit recruitment during neuromuscular electrical stimulation: A critical appraisal. *European Journal of Applied Physiology* 111, 2399-2407 (2011).
5. Towne, C., Montgomery, K. L., Iyer, S. M., Deisseroth, K. & Delp, S. L. Optogenetic control of targeted peripheral axons in freely moving animals. *PLoS One* 8, e72691 (2013).
6. Ji, Z.-G. et al. Light-evoked Somatosensory Perception of Transgenic Rats That Express Channelrhodopsin-2 in Dorsal Root Ganglion Cells. *PLoS One* 7, e32699 (2012).
7. Jacques, S. L. Optical properties of biological tissues: a review. *Phys. Med. Biol.* 58, R37-61 (2013).
8. Kapur, S., Richner, T., Brodnick, S., Williams, J. & Poore, S. Development of an Optogenetic Sensory Peripheral Nerve Interface. *Plast. Surg. Res. Counc.* (2014).
9. Ayling, O. G. S., Harrison, T. C., Boyd, J. D., Goroshkov, A. & Murphy, T. H. Automated light-based mapping of motor cortex by photoactivation of channelrhodopsin-2 transgenic mice. *Nat. Methods* 6, 219-224 (2009).
10. Chuong, A. S. et al. Noninvasive optical inhibition with a red-shifted microbial rhodopsin. *Nat. Neurosci.* 17, 1123-9 (2014).
11. Lin, J. Y., Knutsen, P. M., Muller, A., Kleinfeld, D. & Tsien, R. Y. ReaChR: a red-shifted variant of channelrhodopsin enables deep transcranial optogenetic excitation. *Nat. Neurosci.* 16, 1499-508 (2013).
12. Kim, T., Folcher, M., Baba, M. D.-E. & Fussenegger, M. A Synthetic Erectile Optogenetic Stimulator Enabling Blue-Light-Inducible Penile Erection. *Angew. Chemie* Int. Ed. 54, 5933-5938 (2015).
13. Magown, P., Shettar, B., Zhang, Y. & Rafuse, V. F. Direct optical activation of skeletal muscle fibres efficiently controls muscle contraction and attenuates denervation atrophy. *Nat. Commun.* 6, 8506 (2015).
14. Peterson, E. J. & Tyler, D. J. Motor neuron activation in peripheral nerves using infrared neural stimulation. *J. Neural Eng.* 11, 016001 (2013).
15. BASHKATOV, A. N., GENINA, E. A. & TUCHIN, V. V. OPTICAL PROPERTIES OF SKIN, SUBCUTANEOUS, AND MUSCLE TISSUES: A REVIEW. *J. Innov. Opt. Health Sci.* 04, 9-38 (2011).
16. Yaroslaysky, A. N. et al. Optical properties of selected native and coagulated human brain tissues in vitro in the visible and near infrared spectral range. *Phys. Med. Biol.* 47, 305 (2002).
17. Islam, M. S. et al. Extracting structural features of rat sciatic nerve using polarization-sensitive spectral domain optical coherence tomography. *J. Biomed. Opt.* 17, 056012 (2012).
18. Hendriks, B. H. W. et al. Nerve detection with optical spectroscopy for regional anesthesia procedures. *J. Transl. Med.* 13, 380 (2015).
19. Welch, A. J. & Van Gemert, M. J. C. *Optical-thermal response of laser-irradiated tissue. Optical-Thermal Response of Laser-Irradiated Tissue* (2011). doi:10.1007/978-90-481-8831-4
20. McCartney, C. J. L., Xu, D., Constantinescu, C., Abbas, S. & Chan, V. W. S. Ultrasound examination of peripheral nerves in the forearm. *Reg. Anesth. Pain Med.* 32, 434-9
21. Honjoh, T. et al. Optogenetic Patterning of Whisker-Barrel Cortical System in Transgenic Rat Expressing Channelrhodopsin-2. *PLoS One* 9, e93706 (2014).
22. Cheever, T. R., Olson, E. A. & Ervasti, J. M. Axonal regeneration and neuronal function are preserved in motor neurons lacking??-actin In Vivo. *PLoS One* 6, (2011).
23. Montgomery, K. L. et al. Beyond the brain: Optogenetic control in the spinal cord and peripheral nervous system. *Sci. Transl. Med.* 8, 337rv5 (2016).
24. Bainbridge, J. W. B. et al. Long-Term Effect of Gene Therapy on Leber's Congenital Amaurosis. http://dx-.doi.org/10.1056/NEIMoa1414221 (2015).
25. Mingozzi, F. et al. Immune responses to AAV vectors: overcoming barriers to successful gene therapy. *Blood* 122, 23-36 (2013).
26. Sack, B. K. & Herzog, R. W. Evading the immune response upon in vivo gene therapy with viral vectors. *Curr. Opin. Mol. Ther.* 11, 493-503 (2009).
27. Mason, M. R. et al. Comparison of AAV Serotypes for Gene Delivery to Dorsal Root Ganglion Neurons. *Mol. Ther.* 18, 715-724 (2010).
28. P950035 NeuroControl Freehand System.pdf.
29. Williams, E. K. et al. Sensory Neurons that Detect Stretch and Nutrients in the Digestive System. *Cell* 166, 209-221 (2016).
30. Chang, R. B., Strochlic, D. E., Williams, E. K., Umans, B. D. & Liberles, S. D. Vagal Sensory Neuron Subtypes that Differentially Control Breathing. *Cell* 161, 622-33 (2015).

31. Grosenick, L., Marshel, J. H. & Deisseroth, K. Closed-Loop and Activity-Guided Optogenetic Control. Neuron 86, 106-139 (2015).

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A wearable device for optogenetic motor control and restoring sensation in a mammal, comprising:
   a) a wearable support configured to be positioned at a skin surface and in proximity to a peripheral nerve of the mammal;
   b) a power source at the wearable support;
   c) a transdermal light source configured to direct light toward the peripheral nerve of the mammal while wearing the support, the peripheral nerve being optogenetically altered to functionally express a specific opsin and the light source emitting light at a wavelength required for the specific opsin to respond to illumination; and
   d) a controller at the wearable support and in electrical communication with the power source,
   the controller configured to:
      receive a physiological signal from the mammal; and
      execute closed-loop control of the transdermal light source based on a physiological model linking the received physiological signal to an output signal providing for selective stimulation of the optogenetically altered nerve to induce muscle contraction in the mammal for motor control or to stimulate sensory fibers in the mammal for restoring sensation.

2. The wearable device of claim 1, wherein the wearable support is a strap.

3. The wearable device of claim 2, wherein the strap is a member selected from the group consisting of a wrist strap, a knee strap, a necklace, a headband, ankle strap, leg strap, stomach strap, and an arm strap.

4. The wearable device of claim 1, wherein the wearable support is an adhesive patch.

5. The wearable device of claim 1, wherein the transdermal light source includes at least one member selected from the group consisting of a light emitting diode (LED), diode-pumped solid state (DPSS) laser, diode laser, solid-state laser, vertical-cavity surface emitting laser (VCSEL), and edge emitting laser diode (EELD).

6. The wearable device of claim 1, wherein the light source is of a type that emits a wavelength in a range of between about 300 nm and about 1100 nm.

7. The wearable device of claim 1, further including at least one sensor in communication with the controller, whereby the at least one sensor provides sensory feedback to the controller which controls the light source to thereby selectively stimulate the optogenetically altered nerve.

8. The wearable device of claim 7, wherein the sensory feedback is at least one member of the group consisting of cutaneous feedback and proprioceptive feedback.

9. The wearable device of claim 8, wherein the at least one sensor is selected from the group consisting of an accelerometer, a position sensor, a torque sensor, and a gyroscope.

10. The wearable device of claim 1, wherein the controller includes at least one member of the group consisting of a reflexive controller, a state-based controller, and a pattern-recognition controller.

* * * * *